United States Patent
Mori et al.

(10) Patent No.: US 8,791,293 B2
(45) Date of Patent: Jul. 29, 2014

(54) FLUORINE-CONTAINING SULFONATE, FLUORINE-CONTAINING SULFONATE RESIN, RESIST COMPOSITION AND PATTERN FORMATION METHOD

(75) Inventors: Kazunori Mori, Saitama (JP); Satoru Narizuka, Saitama (JP); Fumihiro Amemiya, Fuchu (JP); Masaki Fujiwara, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/565,259

(22) Filed: Aug. 2, 2012

(65) Prior Publication Data

US 2013/0065182 A1    Mar. 14, 2013

(30) Foreign Application Priority Data

Sep. 8, 2011  (JP) .................. 2011-196308
Jul. 11, 2012  (JP) .................. 2012-155862

(51) Int. Cl.
| C07C 309/10 | (2006.01) |
| C07C 309/06 | (2006.01) |
| C07C 303/22 | (2006.01) |
| G03F 7/004  | (2006.01) |

(52) U.S. Cl.
USPC .......... 562/113; 562/100; 562/108; 562/109; 562/110; 562/111; 562/115; 560/149; 560/183; 560/184; 560/219; 560/220; 430/921; 430/923; 430/925

(58) Field of Classification Search
None
See application file for complete search history.

(56) References Cited

U.S. PATENT DOCUMENTS

| 5,945,250 | A  | 8/1999  | Aoai et al.      |
| 7,812,105 | B2 | 10/2010 | Nagai et al.     |
| 7,956,142 | B2 | 6/2011  | Nagai et al.     |
| 8,227,183 | B2 | 7/2012  | Tsubaki et al.   |
| 2008/0187860 | A1 | 8/2008 | Tsubaki et al.  |
| 2010/0035185 | A1 | 2/2010 | Hagiwara et al. |
| 2011/0015431 | A1 | 1/2011 | Jodry et al.    |
| 2011/0034721 | A1 | 2/2011 | Hagiwara et al. |
| 2011/0112306 | A1 | 5/2011 | Nagamori et al. |
| 2011/0177453 | A1 | 7/2011 | Masubuchi et al.|
| 2012/0058436 | A1 | 3/2012 | Tsubaki et al.  |
| 2012/0270155 | A1* | 10/2012 | Komuro et al. ........... 430/285.1 |
| 2012/0315449 | A1 | 12/2012 | Tsubaki et al. |

FOREIGN PATENT DOCUMENTS

| CA | 2 049 772 A7 | 2/1992 |
| JP | 4-230645 A | 8/1992 |
| JP | 3613491 B2 | 1/2005 |
| JP | 2005-84365 A | 3/2005 |
| JP | 2006-178317 A | 7/2006 |
| JP | 2007-197718 | 8/2007 |
| JP | 2008-133448 A | 6/2008 |
| JP | 2008-292975 A | 12/2008 |
| JP | 2009-7327 A | 1/2009 |
| JP | 2009-91351 A | 4/2009 |
| JP | 2010-18573 A | 1/2010 |
| JP | 2010-95643 A | 4/2010 |
| KR | 10 2011 0069881 A | 6/2011 |
| WO | WO 2006/121096 A1 | 11/2006 |
| WO | WO 2008/056795 A1 | 5/2008 |

OTHER PUBLICATIONS

Korean Office Action dated Jan. 19, 2014 (twenty-nine (29) pages).

* cited by examiner

*Primary Examiner* — Sin J. Lee
(74) *Attorney, Agent, or Firm* — Crowell & Moring LLP

(57) ABSTRACT

According to the present invention, there is provided a fluorine-containing sulfonate resin having a repeating unit of the following general formula (3).

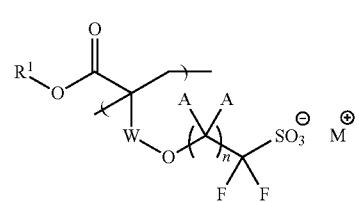

(3)

In order to prevent deficiency such as roughness after pattern formation or failure in pattern formation, the fluorine-containing sulfonate resin incorporates therein a photoacid generating function and serves as a resist resin in which "a moiety capable of changing its developer solubility by the action of an acid" and "a moiety having a photoacid generating function" are arranged with regularity.

10 Claims, No Drawings

FLUORINE-CONTAINING SULFONATE, FLUORINE-CONTAINING SULFONATE RESIN, RESIST COMPOSITION AND PATTERN FORMATION METHOD

FIELD OF THE INVENTION

The present invention relates to a novel polymerizable fluorine-containing sulfonate having an anion structure as well as a fluorine-containing sulfonate resin, a resist composition and a pattern formation method using the same. More particularly, the present invention relates to a resist composition suitably usable as a chemically amplified resist material for fine patterning by high energy radiation, a novel fluorine-containing sulfonate resin for use in the resist composition and a novel fluorine-containing sulfonate for production of the fluorine-containing sulfonate resin.

BACKGROUND OF THE INVENTION

For lithographic pattern formation in semiconductor manufacturing processes, there has been a demand to provide resist compositions with harder resist performance requirements such as, in response to a reduction in wavelength of high energy exposure radiation for fine patterning, a wider depth of focus tolerance (abbreviated as "DOF") than that required under exposure to long wavelength radiation, a small pattern line edge roughness (abbreviated as "LED") and high resolution, in addition to general performance requirements such as high sensitivity, good substrate adhesion and high etching resistance. Chemically amplified resist compositions are being used as resist materials suitable for exposure to such short wavelength radiation. Herein, the chemically amplified resist composition refers to a pattern forming material that contains a photoacid generating agent (referred to as "photoacid generator") capable of generating an acid by irradiation with high energy radiation (referred to as "exposure") and forms a resist pattern by causing a difference in developer solubility between exposed and unexposed portions through a reaction using the acid generated by exposure as a catalyst.

The uniformity of the resist materials is becoming a problem as these pattern forming materials come to practical use in the extreme ultraviolet (EUV) range for finer patterning. More specifically, the resist material is in general conventionally prepared from a resist resin capable of changing its developer solubility by the action of an acid, a solvent and a photoacid generator (as an additive) capable of generating an acid. In such a composition, however, the uniformity of dispersion of the resist resin and the photoacid generator is not sufficient for still finer patterning. It has thus recently been reported to produce a resist resin by copolymerization of a conventional resist raw material monomer with a monomer having a photoacid generating function and thereby impart the photoacid generating function to the resist resin (see Patent Documents 1 to 7). For example, Patent Documents 6 and 7 each disclose a resist composition using a resist resin obtained by polymerization or copolymerization of a methacrylic acid ester whose side chain contains a triphenylsulfonium salt of sulfonic acid having a fluorine atom at α-position thereof.

PRIOR ART DOCUMENTS

Patent Document 1: Japanese Patent No. 3613491
Patent Document 2: International Application Publication No. WO 2006/121096
Patent Document 3: Japanese Laid-Open Patent Publication No. 2006-178317
Patent Document 4: Japanese Laid-Open Patent Publication No. 2007-197718
Patent Document 5: Japanese Laid-Open Patent Publication No. 2008-133448
Patent Document 6: Japanese Laid-Open Patent Publication No. 2009-7327
Patent Document 7: Japanese Laid-Open Patent Publication No. 2010-95643

SUMMARY OF THE INVENTION

With the trend toward fine patterning, the pattern formation methods using high energy radiation, notably ArF excimer laser radiation, far-ultraviolet radiation e.g. EUV or electron beam radiation, would face a problem of deficiency such as roughness after pattern formation or failure in pattern formation due to insufficient resist uniformity.

As mentioned above, it has been attempted to produce the resist resin by the use of the monomer having the photoacid generating function and thereby impart the photoacid generating function to the resist resin for improvement in resist uniformity.

It has however been found by precise composition analysis that, even in this resist resin, "the moiety capable of changing its developer solubility by the action of the acid" and "the moiety with the photoacid generating function" are not arranged regularly. Depending on the production method (polymerization method) of the resist resin, the repeating units based on the respective monomers are not always regularly arranged. In the case where the resist resin has some part in which "the moiety capable of changing its developer solubility by the action of the acid" is not present near "the moiety with the photoacid generating function", such part of the resist resin does not undergo reaction under the catalysis of the acid and becomes a cause of deficiency due to poor pattern formation.

The present inventors have made extensive research to solve the above-mentioned problems and have come up with the idea that, when both of "a moiety with a photoacid generating function" and "a moiety capable of changing its developer solubility by the action of an acid" are incorporated in one molecule of monomer for production of a resist resin, the resulting resist resin allows the acid generated therefrom and the moiety acted upon by the acid to be logically located adjacent to each other at given intervals so as to secure the uniformity of these components.

Based on such an idea, the present inventors have researched specific resins, prepared various polymerizable compounds for production of those polymer resins and made measurements and observations about the resist performance of the produced resins. As a result, the present inventors have found that: a resin having a single repeating unit formed with an acid labile group and a fluorine-containing sulfonate can function in itself as a base resin and as a sulfonic acid onium salt type photoacid generator; and, when the acid labile group and the fluorine-containing sulfonate are contained in different side chains of the resin, a resist composition containing this resin shows higher sensitivity, resolution and mask pattern reproductivity and can foam a pattern with a small LER.

Namely, the present invention includes the following aspects.

[Inventive Aspect 1]
A fluorine-containing sulfonate resin comprising a repeating unit of the following general formula (3):

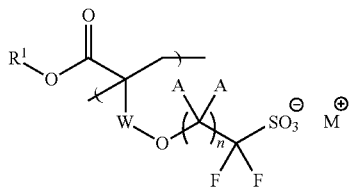
(3)

where A each independently represent a hydrogen atom, a fluorine atom or a trifluoromethyl group; n represents an integer of 1 to 10; W represents a divalent linking group; $R^1$ represents an acid labile group; and $M^+$ represents a monovalent cation.

[Inventive Aspect 2]

The fluorine-containing sulfonate resin according to Inventive Aspect 1, wherein the repeating unit of the general formula (3) is of the following general formula (4):

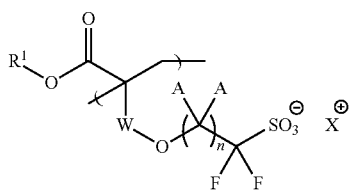
(4)

where A, n, W and $R^1$ have the same definitions as in the general formula (3); and $X^+$ represents either a sulfonium cation of the following general formula (a) or a iodonium cation of the following general formula (b):

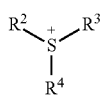
(a)

where $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^2$, $R^3$ and $R^4$ may be bonded together to form a ring with a sulfur atom in the formula,

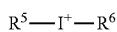
(b)

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula.

[Inventive Aspect 3]

The fluorine-containing sulfonate resin according to Inventive Aspect 1, wherein the repeating unit is of the following general formula (5):

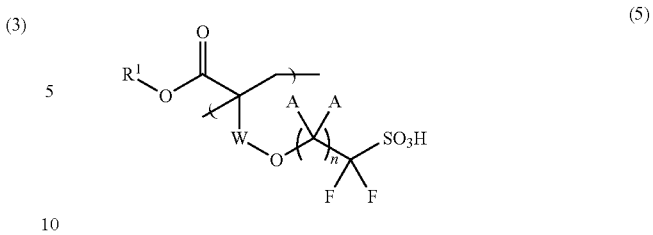
(5)

where A, n, W and $R^1$ have the same definitions as in the general formula (3).

[Inventive Aspect 4]

The fluorine-containing sulfonate resin according to any one of Inventive Aspects 1 to 3, further comprising one or more kinds selected from the group consisting of repeating units formed by cleavage of polymerizable double bonds of olefins, fluorine-containing olefins, acrylic acid esters, methacrylic acid esters, fluorine-containing acrylic acid esters, fluorine-containing methacrylic acid esters, norbornene compounds, fluorine-containing norbornene compounds, styrenic compounds, fluorine-containing styrenic compounds, vinyl ethers and fluorine-containing vinyl ethers.

[Inventive Aspect 5]

The fluorine-containing sulfonate resin according to Inventive Aspect 4, wherein the olefins, the fluorine-containing olefins, the acrylic acid esters, the methacrylic acid esters, the fluorine-containing acrylic acid esters, the fluorine-containing methacrylic acid esters, the norbornene compounds, the fluorine-containing norbornene compounds, the styrenic compounds, the fluorine-containing styrenic compounds, the vinyl ethers and the fluorine-containing vinyl ethers are polymerizable compounds each has, in a molecule thereof, a moiety capable of generating an acid by light irradiation.

[Inventive Aspect 6]

The fluorine-containing sulfonate resin according to Inventive Aspect 4, wherein the olefins, the fluorine-containing olefins, the acrylic acid esters, the methacrylic acid esters, the fluorine-containing acrylic acid esters, the fluorine-containing methacrylic acid esters, the norbornene compounds, the fluorine-containing norbornene compounds, the styrenic compounds, the fluorine-containing styrenic compounds, the vinyl ethers and the fluorine-containing vinyl ethers are polymerizable compounds each has, in a molecule thereof, a moiety capable of being dissociated into an acid by light irradiation.

[Inventive Aspect 7]

The fluorine-containing sulfonate resin according to any one of Inventive Aspects 1 to 6, further comprising a repeating unit of the following general formula (6):

(6)

where $R^7$ represents a hydrogen atom, a halogen atom or a $C_1$-$C_3$ alkyl or fluorine-containing alkyl group; W represents a divalent linking group; and $X^+$ represents either a sulfonium cation of the following general formula (a) or a iodonium cation of the following general formula (b):

(a)

where $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^2$, $R^3$ and $R^4$ may be bonded together to form a ring with a sulfur atom in the formula,

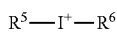
(b)

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula.

[Inventive Aspect 8]

The fluorine-containing sulfonate resin according to any one of Inventive Aspects 1 to 7, further comprising a repeating unit of the following general formula (7):

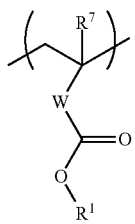
(7)

where $R^7$ represents a hydrogen atom, a halogen atom or a $C_1$-$C_3$ alkyl or fluorine-containing alkyl group; W represents a divalent linking group; and $R^1$ represents an acid labile group.

[Inventive Aspect 9]

The fluorine-containing sulfonate resin according to any one of Inventive Aspects 1 to 8, further comprising a repeating unit of the following general formula (8):

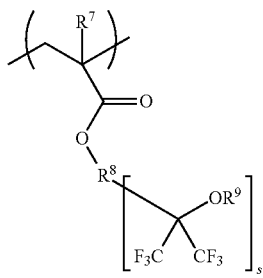
(8)

where $R^7$ represents a hydrogen atom, a halogen atom or a $C_1$-$C_3$ alkyl or fluorine-containing alkyl group; $R^8$ represents a substituted or unsubstituted aliphatic hydrocarbon group, a substituted or unsubstituted aromatic group or an organic group formed by combination of a plurality thereof, in which any number of hydrogen atoms may be substituted with a fluorine atom; $R^9$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, in which any number of hydrogen atoms may be substituted with a fluorine atom, and may contain an ether bond or a carbonyl bond; and s represents an integer of 1 to 2.

[Inventive Aspect 10]

The fluorine-containing sulfonate resin according to any one of Inventive Aspects 1 to 9, further comprising a repeating unit of the following general formula (9):

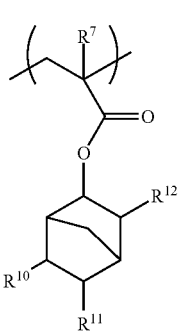
(9)

where $R^7$ represents a hydrogen atom, a halogen atom or a $C_1$-$C_3$ alkyl or fluorine-containing alkyl group; either one of $R^{10}$, $R^{11}$ and $R^{12}$ represents a $CF_3C(CF_3)(OH)CH_2$ group; and the other two of $R^{10}$, $R^{11}$ and $R^{12}$ each represent a hydrogen atom.

[Inventive Aspect 11]

The fluorine-containing sulfonate resin according to any one of Inventive Aspects 1 to 10, further comprising a repeating unit of the following general formula (10):

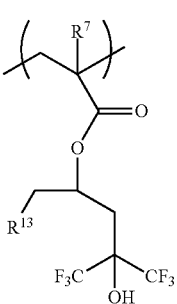
(10)

where $R^7$ represents a hydrogen atom, a halogen atom or a $C_1$-$C_3$ alkyl or fluorine-containing alkyl group; and $R^{13}$ represents a hydrogen atom or a $C_1$-$C_4$ alkyl or fluorine-containing alkyl group.

[Inventive Aspect 12]

The fluorine-containing sulfonate resin according to any one of Inventive Aspects 1 to 11, further comprising a repeating unit of the following general formula (11):

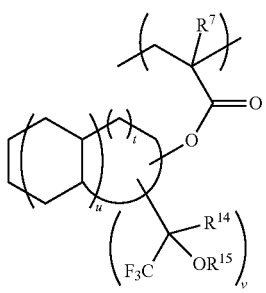

(11)

where $R^7$ represents a hydrogen atom, a halogen atom or a $C_1$-$C_3$ alkyl or fluorine-containing alkyl group; $R^{14}$ represents a methyl group or a trifluoromethyl group; $R^{15}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; u represents an integer of 0 to 2; t and v represent an integer of 1 to 8 and satisfy a relationship of v≤t+2; and, in the case where v is 2 to 8, $R^{14}$, $R^{15}$ may be the same or different.

[Inventive Aspect 13]

The fluorine-containing sulfonate resin according to any one of Inventive Aspects 1 to 11, further comprising a repeating unit of the following general formula (12):

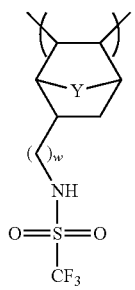

(12)

where Y represents either —CH$_2$—, —O— or —S—; and w represents an integer of 2 to 6.

[Inventive Aspect 14]

The fluorine-containing sulfonate resin according to any one of Inventive Aspects 1 to 13, further comprising either a repeating unit of the following general formula (13) or a repeating unit of the following general formula (13-1):

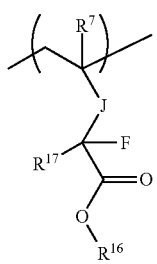

(13)

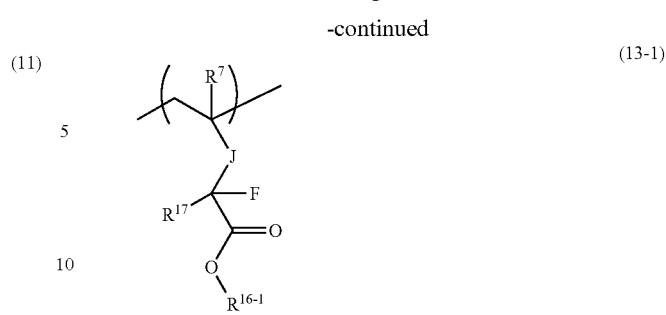

(13-1)

where $R^7$ represents a hydrogen atom, a halogen atom or a $C_1$-$C_3$ alkyl or fluorine-containing alkyl group; $R^{17}$ represents a hydrogen atom, a fluorine atom or a fluorine-containing alkyl group; J represents a divalent linking group; $R^{16}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; and $R^{16-1}$ represents an acid labile group.

[Inventive Aspect 15]

The fluorine-containing sulfonate resin according to any one of Inventive Aspects 1 to 14, further comprising a repeating unit of the following general formula (14):

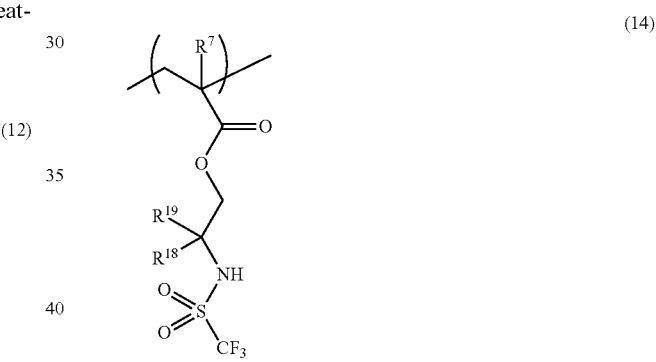

(14)

where $R^7$ represents a hydrogen atom, a halogen atom or a $C_1$-$C_3$ alkyl or fluorine-containing alkyl group; and $R^{18}$ and $R^{19}$ each independently represent a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group.

[Inventive Aspect 16]

A resist composition comprising at least the fluorine-containing sulfonate resin according to any one of Inventive Aspects 1 to 15 and a solvent.

[Inventive Aspect 17]

The resist composition according to Inventive Aspect 16, further comprising a resin having an acid labile group so that the resist composition serves as a chemically amplified positive resist composition.

[Inventive Aspect 18]

The resist composition according to Inventive Aspect 16 or 17, further comprising a compound capable of generating an acid by radiation so that the resist composition serves as a chemically amplified positive resist composition.

[Inventive Aspect 19]

A pattern formation method, comprising: applying the resist composition according to any one of Inventive Aspects 16 to 18 to a substrate; heat treating the applied resist composition and exposing the heat treated resist composition to high energy radiation of 300 nm or less wavelength through a photomask; and, after optionally heat treating the exposed resist composition, developing the exposed resist composition with a developer.

[Inventive Aspect 20]

The pattern formation method according to Inventive Aspect 19, wherein the exposing is performed, with the use of ArF excimer laser radiation of 193 nm wavelength, by liquid immersion lithography in which water or any liquid medium other than water, having a higher refractive index than air, is inserted between the substrate to which the resist composition has been applied and a projection lens.

[Inventive Aspect 21]

The pattern formation method according to Inventive Aspect 20, wherein the exposing is performed with the use of soft X-ray radiation (EUV radiation) of 10 to 14 nm wavelength.

[Inventive Aspect 22]

A polymerizable fluorine-containing sulfonic acid or sulfonate having an anion structure of the following general formula (1):

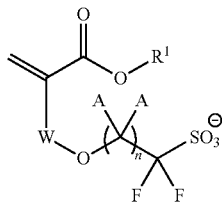

(1)

where A each independently represent a hydrogen atom, a fluorine atom or a trifluoromethyl group; n represents an integer of 1 to 10; W represents a divalent linking group; and $R^1$ represents an acid labile group.

[Inventive Aspect 23]

The polymerizable fluorine-containing sulfonate according to Inventive Aspect 22, wherein the polymerizable fluorine-containing sulfonate is a polymerizable fluorine-containing sulfonic acid onium salt of the following general formula (2):

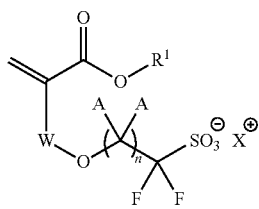

(2)

where A, n, W and $R^1$ have the same definitions as in the general formula (1); and $X^+$ represents either a sulfonium cation of the following general formula (a) or a iodonium cation of the following general formula (b):

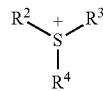

(a)

where $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^2$, $R^3$ and $R^4$ may be bonded together to form a ring with a sulfur atom in the formula,

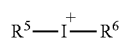

(b)

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula.

[Inventive Aspect 24]

A production method of a polymerizable fluorine-containing sulfonic acid onium salt of the general formula (2), comprising causing condensation of an acrylic acid derivative of the following general formula (15) and a hydroxyalkanesulfonic acid onium salt of the following general formula (16) in the presence of a base catalyst,

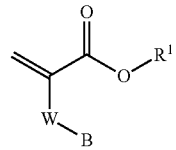

(15)

where W represents a divalent linking group; $R^1$ represent an acid labile group; and B represents a halogen atom or a leaving group,

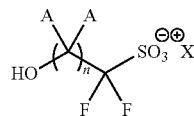

(16)

where A each independently represent a hydrogen atom, a fluorine atom or a trifluoromethyl group; n represents an integer of 1 to 10; $X^+$ represents either a sulfonium cation of the following general formula (a) or a iodonium cation of the following general formula (b):

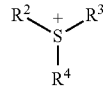

(a)

where $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^2$, $R^3$ and $R^4$ may be bonded together to form a ring with a sulfur atom in the formula,

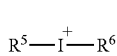
(b)

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula,

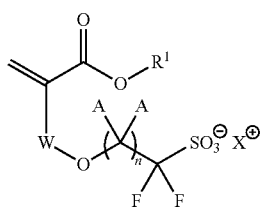
(2)

where A, n, W, $R^1$ and $X^+$ have the same definitions as in the general formulas (15) and (16).

[Inventive Aspect 25]

The production method according to Inventive Aspect 24, wherein W is methylene in the acrylic acid derivative of the general formula (15).

[Inventive Aspect 26]

The production method according to Inventive Aspect 24 or 25, wherein the acrylic acid derivative of the general formula (15) is of the following general formula (17) or (18):

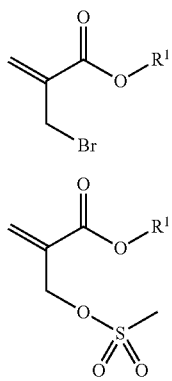
(17)
(18)

where $R^1$ has the same definition as in the general formula (15).

[Inventive Aspect 27]

The production method according to any one of Inventive Aspects 24 to 26, wherein the acrylic acid derivative of the general formula (15) is either tert-butyl 2-(bromomethyl)acrylate, 2-methyladamantyl 2-[(methanesulfonyloxy)methyl]acrylate or 1-methylcyclopentyl 2-[(methanesulfonyloxy)methyl]acrylate.

[Inventive Aspect 28]

The production method according to Inventive Aspect 24, wherein n is 1 and A is hydrogen in the hydroxyalkanesulfonyl acid onium salt of the general formula (16).

[Inventive Aspect 29]

The production method according to Inventive Aspect 24, wherein $X^+$ is triphenylsulfonium in the hydroxyalkanesulfonyl acid onium salt of the general formula (16).

The resist resin according to the present invention, in which both of the acid labile group and the fluorine-containing sulfonate structure are incorporated in one repeating unit, function as a sulfonic acid onium salt type photoacid generator and as a resin capable of changing its developer solubility. In the resist resin, "the moiety with the photoacid generating function" and "the moiety capable of chaining its developer solubility by the action of the acid" are arranged adjacent to each other so as to thereby avoid lack of uniformity in the resin, which becomes a cause of deficiency, and prevent the acid labile group from being left (remaining) unreacted due to insufficient regularity. It is therefore possible to obtain significant effects such as high sensitivity, high resolution, high mask pattern reproductivity and small LER in pattern formation. It is also possible to adjust the resin properties such as acidity of sulfonic acid generated, boiling point, solubility and acid decomposition temperature by varying combination of the acid generating group and the acid labile group. In the present invention, one or two or more of the above significant effects can be obtained.

DESCRIPTION OF EMBODIMENTS

Hereinafter, embodiments of the present invention will be described below in detail. It should be however understood that: the present invention is not limited to the following embodiments; various changes and modifications can be made on the following embodiments as appropriate, without departing from the scope of the present invention, based on the ordinary knowledge of those skilled in the art.

In the section "DESCRIPTION OF EMBODIMENTS" of the present specification, the braces "[ ]" and "⟨ ⟩" are merely symbols and do not have meanings in themselves.

Further, the following terms have the following meanings in the present specification. The term "base resin" means a resin capable of changing its developer solubility by exposure and, unless otherwise specified, refers to a resin having a positive resist function in the present specification. The term "positive resist" means a resist whose exposed portion is more soluble in a developer than its unexposed portion. Unless otherwise specified, the term "salt" includes the case where $H^+$ is a cation of the salt.

A material relationship of the present invention is indicated in Scheme (1).

Scheme (1)

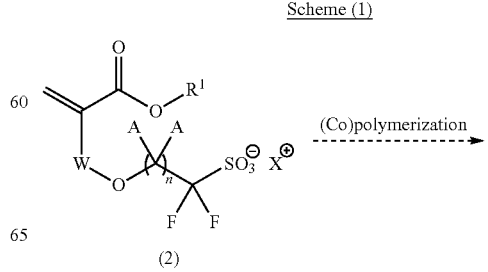
(2)

-continued

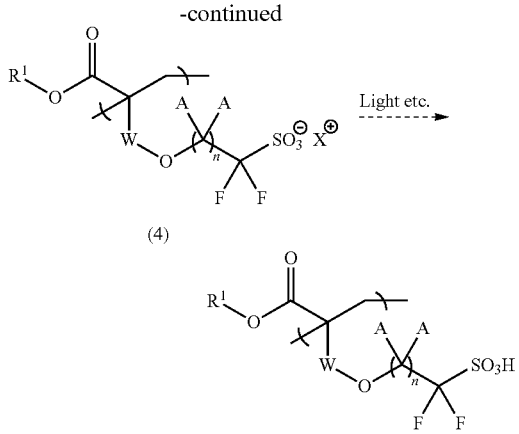

A sulfonate resin having a repeating unit of the general formula (4) is obtained by homopolymerization or copolymerization of a polymerizable fluorine-containing sulfonic acid onium salt of the general formula (2) and is converted to a resin having a repeating unit of the general formula (5) by the action of high energy radiation, heat etc. The resulting fluorine-containing sulfonic acid functions as an acid catalyst.

[Polymerizable Fluorine-Containing Sulfonic Acid or Sulfonate]

A polymerizable fluorine-containing sulfonic acid or sulfonate having an anion structure of the general formula (1) will be first described below.

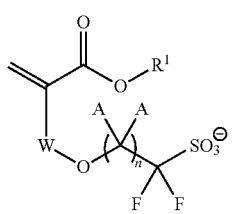

The polymerizable fluorine-containing sulfonic acid or sulfonate having the anion structure of the general formula (1) can be in the form of a polymerizable fluorine-containing sulfonic acid or sulfonate of the general formula (1-1).

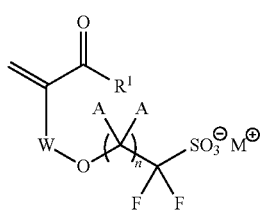

In the general formula (1-1), M$^+$ represents a monovalent cation such as a proton, a metal cation, e.g., lithium ion, sodium ion or potassium ion, or an onium ion, e.g., ammonium ion, sulfonium ion, iodonium ion or phosphonium ion.

In the general formula (1) and in the general formula (1-1), A each independently represent a hydrogen atom, a fluorine atom or a trifluoromethyl group; n represents an integer of 1 to 10, preferably an integer of 1 to 6; W represents a divalent linking group; and R$^1$ represents an acid labile group.

The structure represented by —(CA$_2$)$_n$— in the general formula (1) and in the general formula (1-1) is thus a C$_1$-C$_{10}$ straight alkylene group in which any number of hydrogen atoms may be substituted with a fluorine atom. Among others, preferred are those represented by —(CH$_2$)$_p$—(CF$_2$)$_q$— where p represents an integer of 0 to 10; and q represents an integer of 0 to 8. It is preferable that p is an integer of 1 to 6 and q is an integer of 0 to 5. It is more preferable that p is an integer of 1 to 4 and q is 0 or 1.

The resin in which the sulfonic acid onium salt is fixed as a chemically amplified photoacid generating moiety to the polymer side chain characteristically shows a wide DOF and a small LER as the diffusion length of the generated acid is substantially limited. The ease of diffusion and diffusion length of the acid can be adjusted by controlling the chemical structure of the linking group between the main chain and the acid moiety and the length of the side chain of the resin.

<Linking Group W>

The divalent linking group W is a substituted or unsubstituted methylene group, a substituted or unsubstituted divalent alicyclic hydrocarbon group, a divalent aromatic hydrocarbon group and a substituted or unsubstituted divalent heterocyclic group or a divalent linking group formed by combination of one kind or two or more kinds selected from the group consisting of the above linking groups, an etheric oxygen atom, an etheric sulfur atom, a carbonyl group, an ester group, an oxycarbonyl group, an amide group, a sulfoneamide group, an urethane group, an urea group and the like. Any number of hydrogen atoms bonded to carbon atoms of the divalent linking group may be substituted with a fluorine atom. Any carbon atoms may form a ring with or without a substituent in the divalent linking group.

The substituted methylene group, as the constituent of the divalent linking group W, is represented by the following general formula (c).

Although there is no particular limitation on the monovalent group R$^{19}$, R$^{20}$ in the substituted methylene group, R$^{19}$ and R$^{20}$ each independently represent a hydrogen atom, a halogen atom, a hydroxy group or a monovalent C$_1$-C$_{30}$ group selected from the group consisting of a substituted or unsubstituted alkyl group, a substituted or unsubstituted aliphatic hydrocarbon group, a substituted or unsubstituted alkoxy group, a substituted or unsubstituted aryl group and a substituted or unsubstituted condensed polycyclic aromatic group, which may contain a fluorine atom, an oxygen atom, a sulfur atom, a nitrogen atom or a carbon-carbon double bond. Further, R$^{19}$ and R$^{20}$ may be the same or different and may form a ring structure, preferably an alicyclic hydrocarbon structure, with any atom in the molecule. The monovalent organic group as R$^{19}$, R$^{20}$ is exemplified as follows.

The unsubstituted acyclic alkyl group as R$^{19}$, R$^{20}$ is of 1 to 30 carbon atoms, preferably 1 to 12 carbon atoms. Examples of the unsubstituted acyclic alkyl group as R$^{19}$, R$^{20}$ are methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl. In the present specification, the term "lower" means that the group to which the term is attached has 1 to 4 carbon atoms and, in the case where the group is cyclic, has 3 to 7 carbon atoms.

The substituted acyclic alkyl group as R$^{19}$, R$^{20}$ is one obtained by substitution of one hydrogen atom or two or more hydrogen atoms of the above alkyl group with a $C_1$-$C_4$ alkoxy group, a halogen atom, an acyl group, an acyloxy group, a cyano group, a hydroxy group, a carboxy group, an alkoxycarbonyl group, a nitro group or the like. A fluorine-substituted alkyl group, i.e., fluoroalkyl group is preferred. Examples of the substituted acyclic alkyl group as $R^{19}$, $R^{20}$ are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

The alicyclic hydrocarbon group as $R^{19}$, $R^{20}$ or the alicyclic hydrocarbon group formed by $R^{19}$ and $R^{20}$ together with the carbon atom bonded thereto may be monocyclic or polycyclic. Examples of the alicyclic hydrocarbon group are those having a monocyclo, bicyclo, tricycle or tetracyclo structure of 3 or more carbon atoms, preferably 3 to 30 carbon atoms, more preferably 3 to 25 carbon atoms. The alicyclic hydrocarbon group may be substituted or unsubstituted. As the monocyclic hydrocarbon group, there can preferably be used those having 3 to 12 ring carbon atoms, more preferably 3 to 7 ring carbon atoms. Specific examples of the monocyclic hydrocarbon group are cyclopropyl, cyclobutyl, cyclopentyl, cyclohexyl, cycloheptyl, cyclooctyl, cyclodecanyl, cyclododecanyl, and 4-tert-butylcyclohexyl. As the polycyclic hydrocarbon group, there can preferably be used those having 7 to 15 ring carbon atoms. Specific examples of the polycyclic hydrocarbon group are adamantyl, noradamantyl, decalin residue, tricyclodecanyl, tetracyclododecanyl, norbornyl and cedrol. The alicyclic hydrocarbon group can be in the form of a spiro ring preferably having 3 to 6 carbon atoms. Preferred examples of the spiro ring are adamantyl, decalin residue, norbornyl, cedrol, cyclohexyl, cycloheptyl, cyclooctyl, cyclodecanyl, cyclododecanyl and tricyclodecanyl. One or two or more hydrogen atoms on the ring carbons of the above organic group or the above linking group may be each independently substituted with a substituent such as $C_1$-$C_{30}$ alkyl or substituted alkyl group, hydroxy group, alkoxy group, carboxyl group or alkoxycarbonyl group. One or two or more hydrogen atoms of the substituent may further be substituted with fluorine or trifluoromethyl.

Herein, the $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxy group and the like. The alkoxy group is, for example, a $C_1$-$C_4$ alkoxy group such as methoxy, ethoxy, propoxy or butoxy. The alkoxy carbonyl group is, for example, methoxycarbonyl, ethoxycarbonyl or isopropoxycarbonyl.

Examples of the alkoxy group as $R^{19}$, $R^{20}$ are those of 1 to 4 carbon atoms, such as methoxy, ethoxy, propoxy and butoxy.

The substituted or unsubstituted aryl group as $R^{19}$, $R^{20}$ is of 1 to 30 carbon atoms. The aryl group, when it is monocyclic, preferably has 3 to 12 ring carbon atoms, more preferably 3 to 6 ring carbon atoms. Examples of the substituted or unsubstituted aryl group as $R^{19}$, $R^{20}$ are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the substituted or unsubstituted $C_1$-$C_{30}$ condensed polycyclic aromatic group are monovalent organic groups obtained by elimination of one hydrogen atom from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One hydrogen atom or two or more hydrogen atoms of the above condensed polycyclic aromatic group may preferably be substituted with a fluorine atom or a $C_1$-$C_4$ alkyl or fluorine-containing alkyl group.

Examples of the heteroatom-containing group are monocyclic or polycyclic heterocyclic groups of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One hydrogen atom or two or more hydrogen atoms on the ring structure of the above heterocyclic group may be each independently substituted with an alkyl group, an alicyclic hydrocarbon group, an aryl group or a heterocyclic group. Among others, preferred are those having a monocyclic or polycyclic ether ring or lactone ring structure as represented by the following general formula (d).

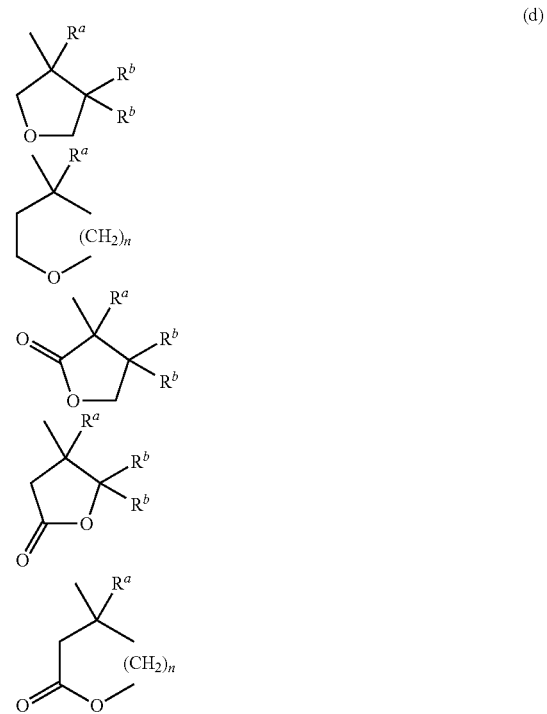

(d)

In the general formula (d), $R^a$ and $R^b$ each independently represent a hydrogen atom or a $C_1$-$C_4$ alkyl group; and n represents an integer of 2 to 4.

The divalent alicyclic hydrocarbon group, constituting the main skeleton of the linking group W, can be either monocyclic or polycyclic. More specifically, the divalent alicyclic hydrocarbon group can be formed with a monocyclo, bicycle, tricycle or tetracyclo structure of 3 or more carbon atoms, preferably 3 to 30 carbon atoms, more preferably 3 to 25 carbon atoms. Further, the divalent alicyclic hydrocarbon group may be substituted or unsubstituted. The alicyclic hydrocarbon group, when it is monocyclic, preferably has 3 to 12 ring carbon atoms, more preferably 3 to 7 ring carbon atoms. Examples of the monocyclic alicyclic hydrocarbon group are cyclopropylene, cyclobutylene, cyclopentylene, cyclohexylene, cycloheptylene, cyclooctylene, cyclodecanylene, cyclododecanylene and 4-tert-butylcyclohexylene. The alicyclic hydrocarbon group, when it is polycyclic, has e.g. 7 to 15 ring carbon atoms. Examples of the polycyclic alicyclic hydrocarbon group are adamantylene, noradamantylene, divalent decalin residue, tricyclodecanylene, tetracyclododecanylene, norbornylene and divalent cedrol residue. The alicyclic hydrocarbon group can be in the form of a spiro ring preferably of 3 to 6 carbon atoms. One or two or more of hydrogen atoms on the ring carbons of the above organic group or the above linking group may be each independently substituted with a substituent such as $C_1$-$C_{30}$ alkyl group or substituted alkyl group, hydroxy group, alkoxyl group, carboxyl group or alkoxycarbonyl group.

As the substituent, the $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxyl group and the like. The alkoxyl group is, for example, a $C_1$-$C_4$ alkoxyl group such as methoxy, ethoxy, propoxy or butoxy. The alkoxycarbonyl group is, for example, methoxycarbonyl, ethoxycarbonyl or isopropoxycarbony.

The divalent aromatic hydrocarbon group, constituting the main skeleton of the linking group W, can be in the form of a monocyclic or condensed polycyclic aromatic ring structure of 1 to 30 carbon atoms. The monocyclic aromatic hydrocarbon group preferably has 3 to 12 ring carbon atoms, more preferably 3 to 6 ring carbon atoms. Examples of the monocyclic aromatic hydrocarbon group are divalent groups obtained by elimination of two hydrogen atoms from benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene and the like. The condensed polycyclic aromatic hydrocarbon group can be substituted or unsubstituted and preferably has 1 to 30 carbon atoms. Examples of the condensed polycyclic aromatic hydrocarbon group are divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene etc. One or two or more of hydrogen atoms of the above divalent organic group may be each independently substituted with a fluorine atom or a $C_1$-$C_4$ alkyl group or fluorine-containing alkyl group.

The heterocyclic group, constituting the main skeleton of the linking group W, can be in the form of a monocyclic or polycyclic ring structure of 3 to 25 ring carbon atoms. The ring structure may be aromatic or nonaromatic. Examples of the heterocyclic group are divalent organic groups obtained by elimination of two hydrogen atoms from pyridine, furan, thienine, pyranine, pyrroline, thianthrene, pyrazon, isothiaz-one, isooxazone, pyrazine, pyrimidine, pyridazine, tetrahydropyranine, tetrahydrofuranine, tetrahydrothiopyranine, tetrahydrothiofuranine and the like. One or two or more of hydrogen atoms on the ring structure of the above divalent organic group may be each independently substituted with an alkyl group (preferably, a lower alkyl group), an alicyclic hydrocarbon group, an aryl group or a heterocyclic group. Among others, preferred are monocyclic or polycyclic ether rings as represented by the following formula (e). In the formula (e), open-ended lines indicate uncombined hands.

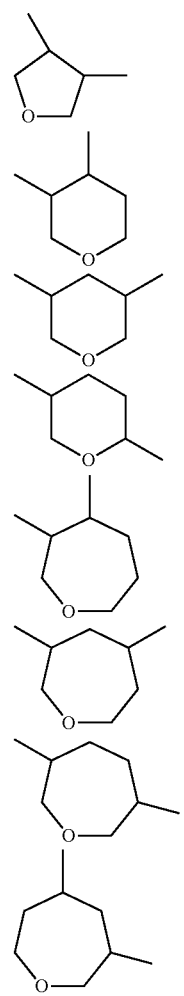

(e)

As mentioned above, the divalent linking group W may formed by combination of any of the divalent groups explained above by the general formulas or specifically exemplified above. In particular, the linking group W is preferably alkylene. Preferred examples of the alkylene group as the linking group W are those represented by the formula (e-1).

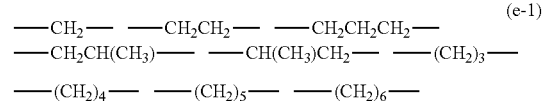

(e-1)

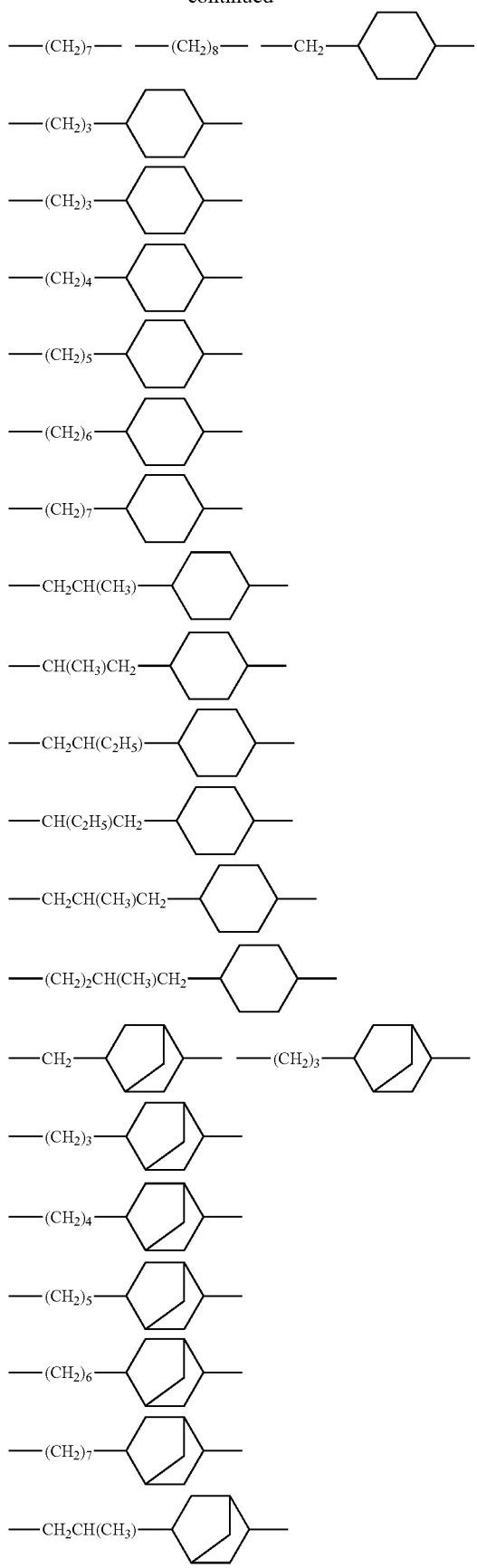

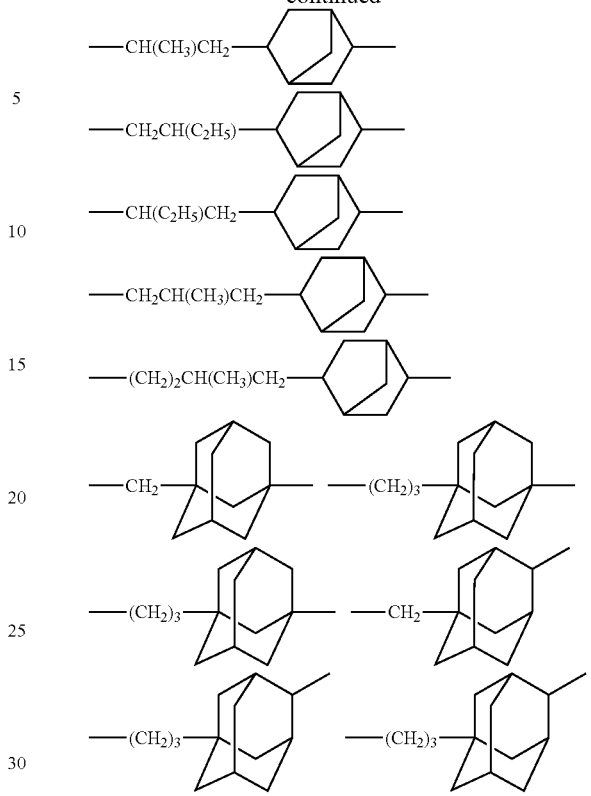

<Acid Labile Group>

Next, $R^1$ will be explained below. Herein, $R^1$ is either one of acid labile groups represented by the following general formulas (f) to (j).

$$R^{X1}-O-C(=O)- \tag{f}$$

$$R^{X1}-O-CHR^{X2}- \tag{g}$$

$$CR^{X3}R^{X4}R^{X5}- \tag{h}$$

$$SiR^{X3}R^{X4}R^{X5}- \tag{i}$$

$$R^{X1}-C(=O)- \tag{j}$$

In the general formulas (d) to (j), $R^{X1}$ represents an alkyl group, an alicyclic hydrocarbon group or an aryl group; $R^{X2}$ represents a hydrogen atom, an alkyl group, an alicyclic hydrocarbon group, an alkenyl group, an aralkyl group, an alkoxy group or an aryl group; $R^{X3}$, $R^{X4}$ and $R^{X5}$ may be the same or different and each represent an alkyl group, an alicyclic hydrocarbon group, an alkenyl group, an aralkyl group or an aryl group; and two of $R^{X3}$, $R^{X4}$ and $R^{X5}$ may be bonded together to form a ring. In each of $R^{X1}$ to $R^{X5}$, any carbon atom may be replaced by an oxygen atom (ether group); and any methylene group may be replaced by a carbonyl group.

Preferred examples of the alkyl group are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, norbornanepoxy, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, toluoyl, cumenyl, naphthyl and anthracenyl. These groups may each have a substituent. Preferred examples of the aralkyl group are those of 7 to 20 carbon atoms, such as benzyl, phenethyl and cumyl, which may each have a substituent.

As the substituent, there can be used: a hydroxy group; a halogen atom (fluorine, chlorine, bromine, iodine); a nitro group; a cyano group; any of the above alkyl or alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (k-1) and (k-2) as the substituent.

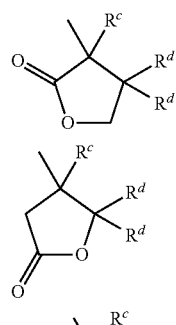

(k-1)

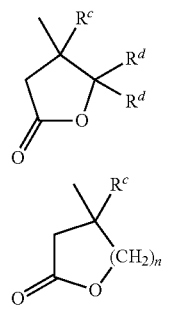

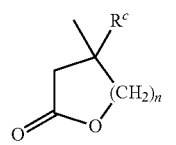

(k-2)

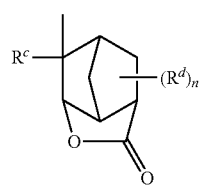

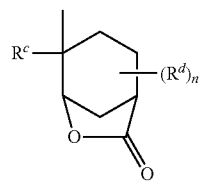

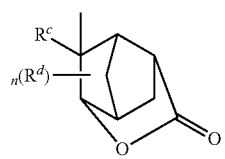

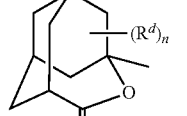

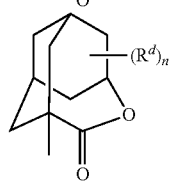

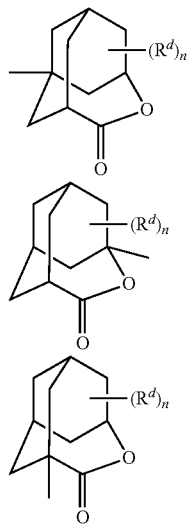

In the formulas (k-1) and (k-2), $R^c$ represents a $C_1$-$C_4$ alkyl or perfluoroalkyl group; $R^d$ each independently represent a hydrogen atom, a $C_1$-$C_4$ alkyl or perfluoroalkyl group, a hydroxy group, a carboxylic acid group, an alkyloxycarbonyl group, an alkoxy group or the like; and n represents an integer of 1 to 4.

Among others, the acid labile group of the general formula (d), (e) or (f) is particularly preferred for use in a resist composition for pattern formation by exposure to high energy radiation such as laser radiation or electron beam radiation because each of the acid labile groups of the general formulas (f), (g) and (h) performs a chemical amplification function.

The acid labile group is more specifically exemplified as follows.

Specific examples of the alkoxycarbonyl group represented by the general formula (f): $R^{X1}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantanoxycarbonyl.

Specific examples of the acetal group represented by the general formula (g): $R^{X1}$—O—CHR$^{X2}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the hydrocarbon group represented by the general formula (h): $CR^{X3}R^{X4}R^{X5}$— are i-propyl, sec-butyl, i-butyl, tert-butyl, tert-amyl, trifluoromethyl, 2,2,2-trifluoroethyl, 3,3,3-trifluoropropyl, hexafluoroisopropanol, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

Specific examples of the alicyclic hydrocarbon group or the alicyclic hydrocarbon-containing acid labile group are those represented by the following formulas (1-1) and (1-2).

(1-1)

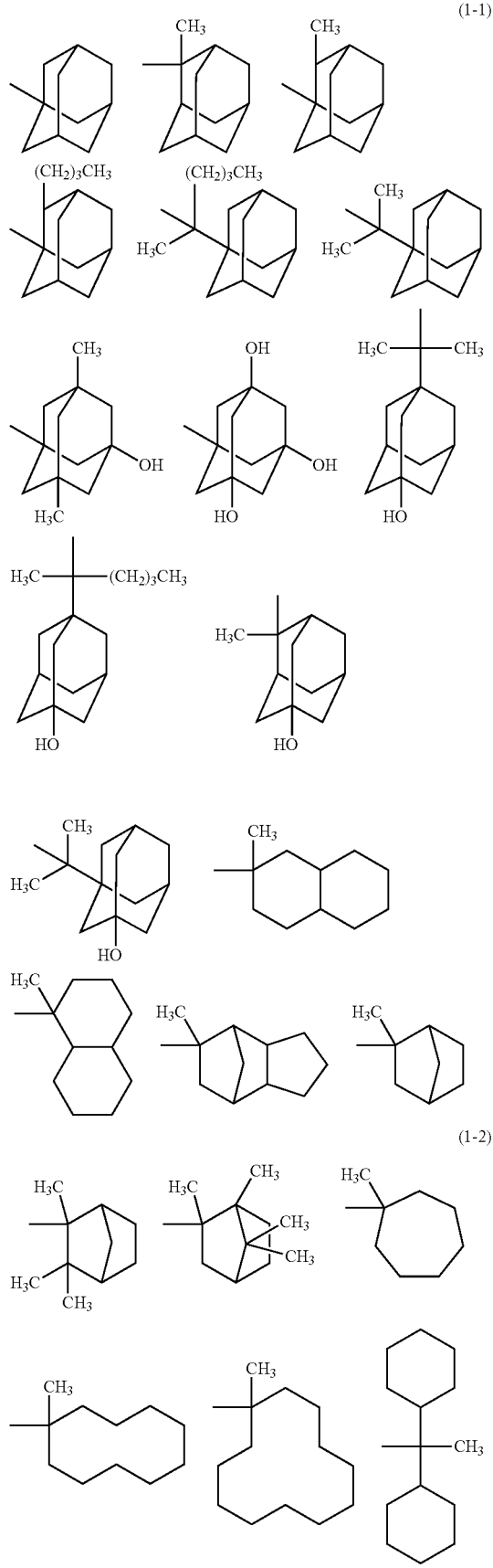

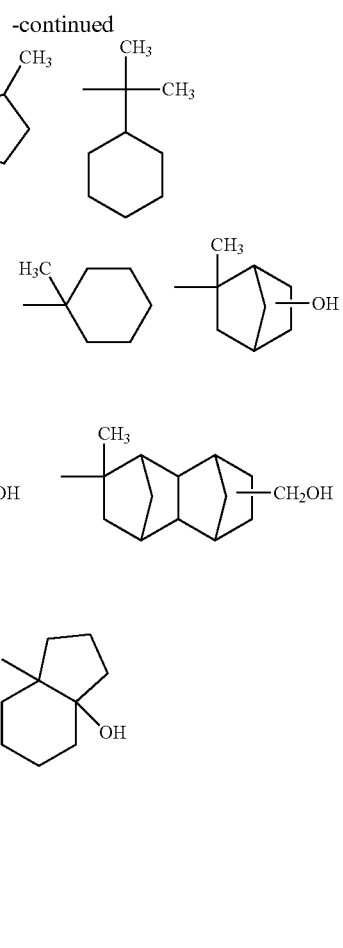

(1-2)

In the formulas (1-1) and (1-2), methyl ($CH_3$) group may independently be replaced by ethyl group ($CH_3CH_2$). One or two or more of the ring carbons may have a substituent as mentioned above.

Specific examples of the silyl group represented by the general formula (1): $SiR^{X3}R^{X4}R^{X5}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (j): $R^{X1}$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydroatropoyl, atropoyl, cinnamoyl, furoyl, thenoyl, nicotinoyl and isonicotinoyl. There can also be used those obtained by substitution of a part or all of hydrogen atoms of the above acid labile groups with a fluorine atom.

Specific examples of the lactone-containing acid-labile protecting group are those represented by the following formulas (m), (n) and (o).

(m)
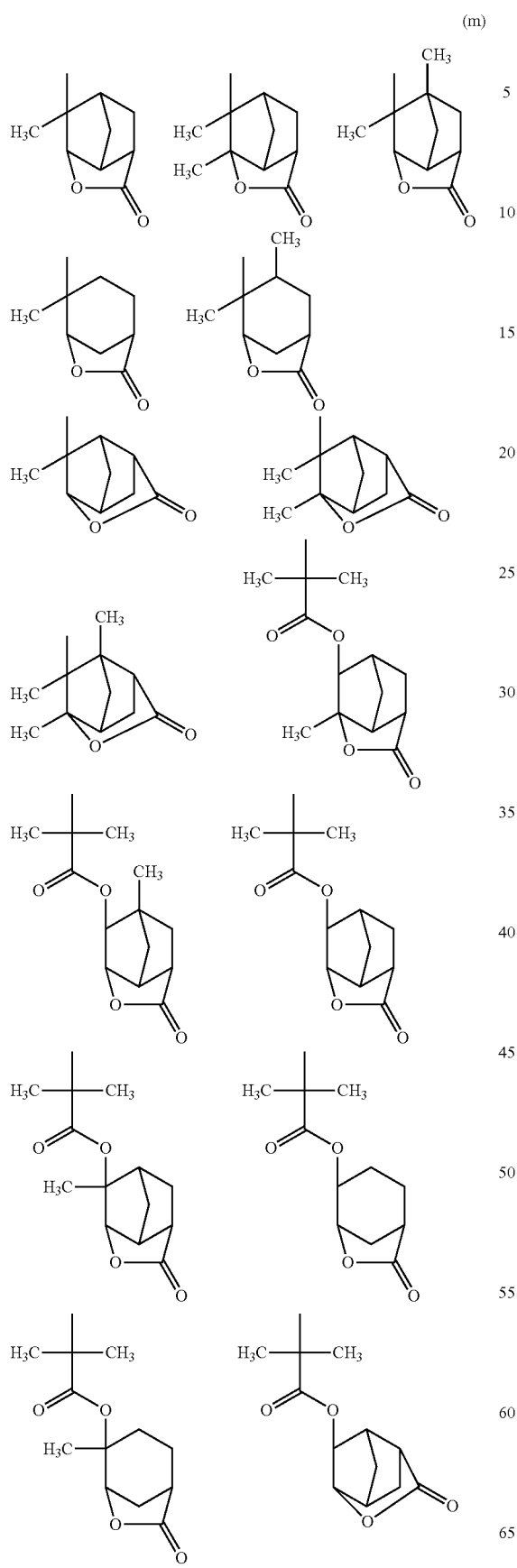
-continued
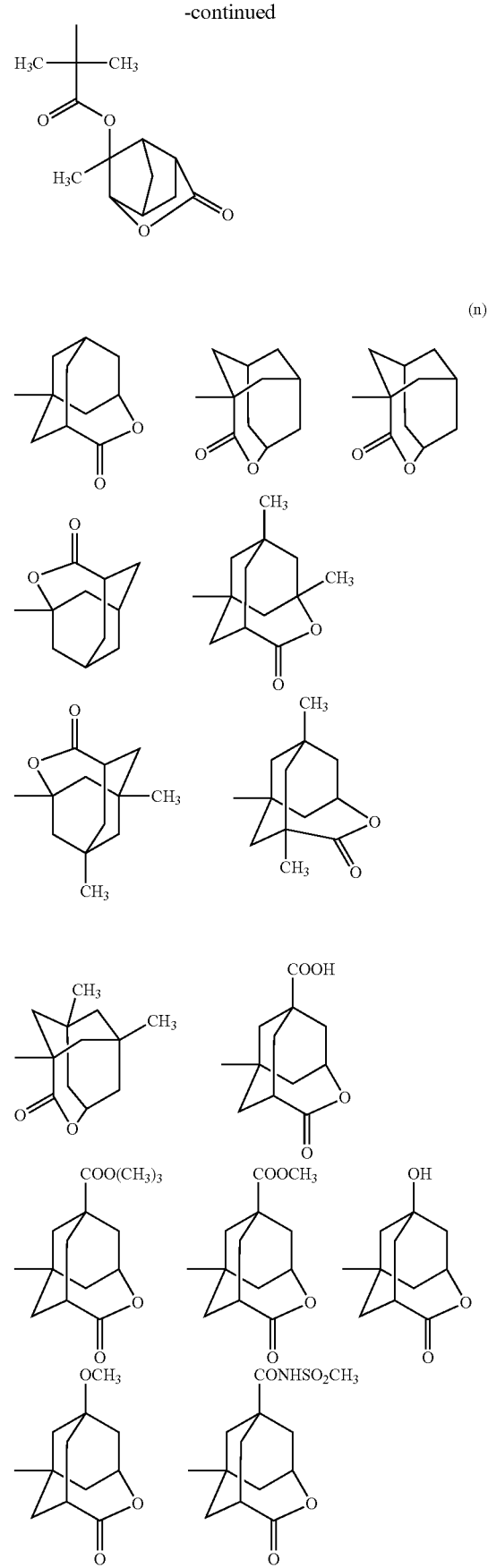
(n)

-continued

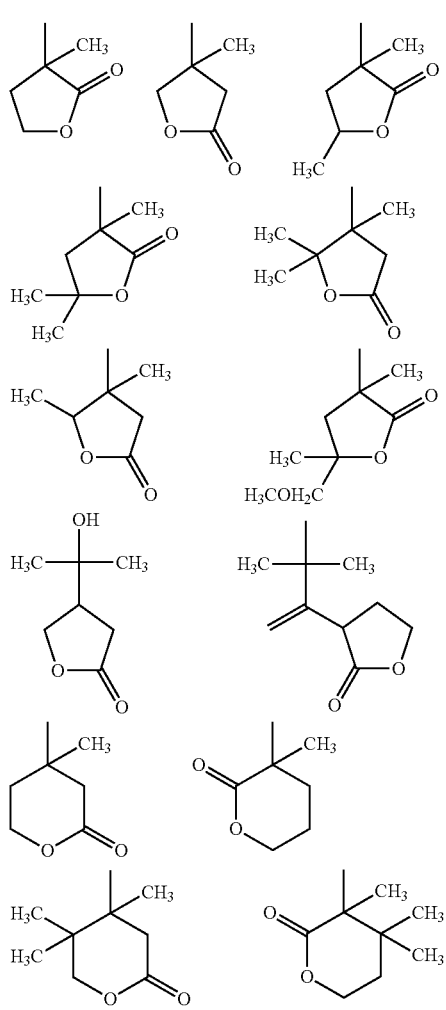

(o)

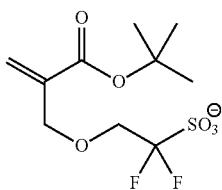
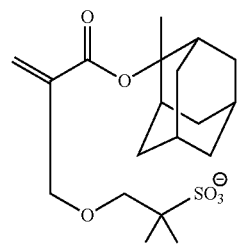

(p-1)

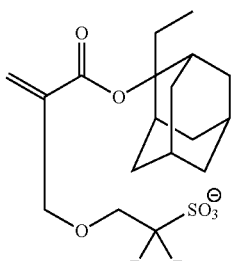
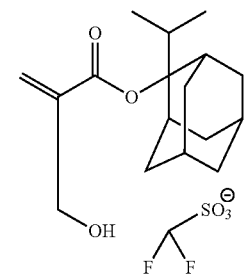

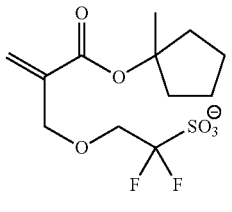
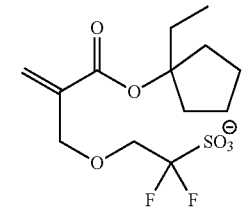

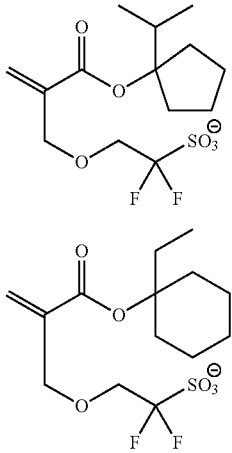
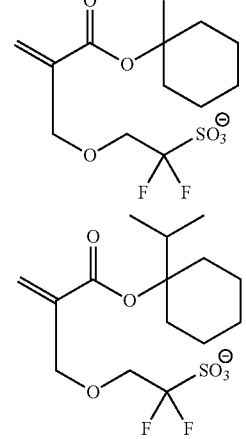

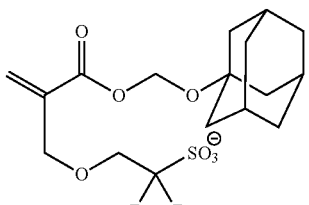

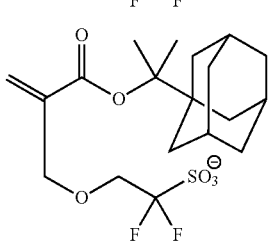

In the formulas (m), (n) and (o), methyl ($CH_3$) group may independently be replaced by ethyl group ($CH_3CH_2$).

In the case of using an ArF excimer laser as an exposure light source, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an alicyclic hydrocarbon such as adamantyl or isobornyl, an alicyclic hydrocarbon-containing acid labile group containing or a lactone-containing acid labile group as exemplified above.

<Anion Structure of General Formula (1)>

The following are specific examples of the anion structure of the general formula (1). Specific examples of the fluorine-containing sulfonate of the general formula (1-1) are those in which the cation $M^+$ is bonded to the following anion structures. Specific examples of the fluorine-containing sulfonic acid onium salt of the general formula (2) are those in which the cation $Q^+$ is bonded to the following anion structures. Although these examples correspond to the case where the linking group W is methylene in the general formula (1), (1-1), (2), there can particularly preferably be used those containing the alkylene groups of the general formula (e-1) as the linking group W.

29
-continued
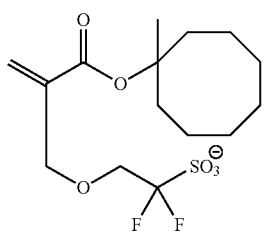
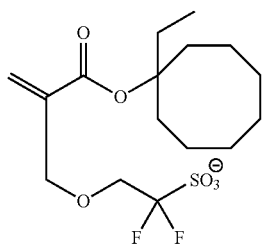
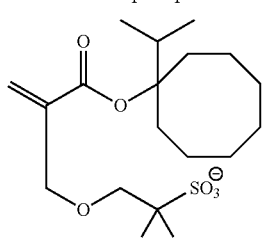
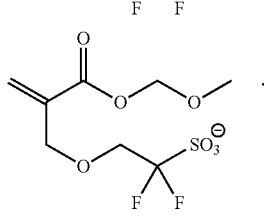
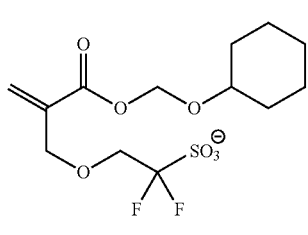
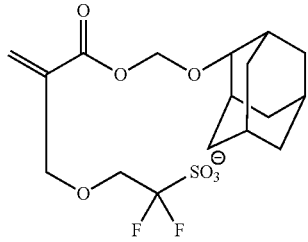
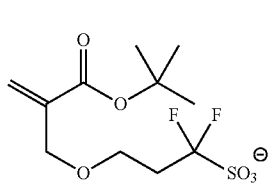
30
-continued
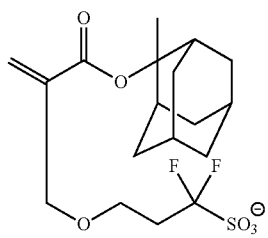
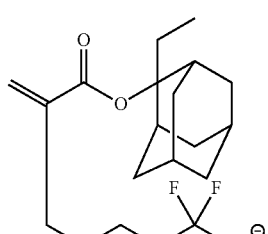
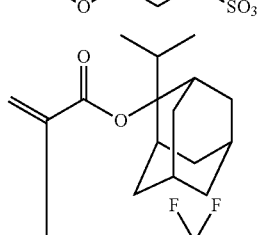
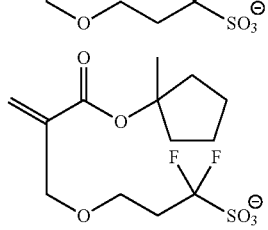
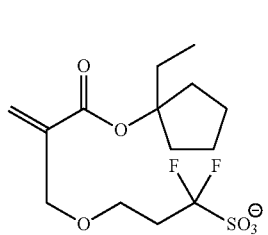
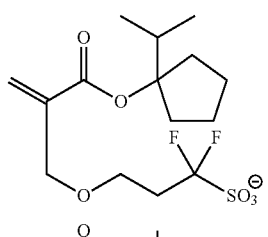
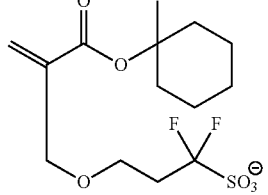
(p-2)

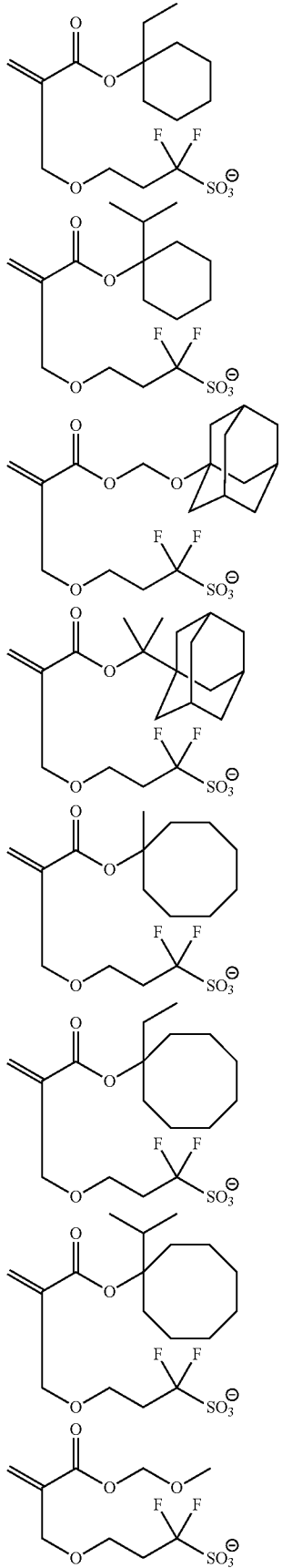
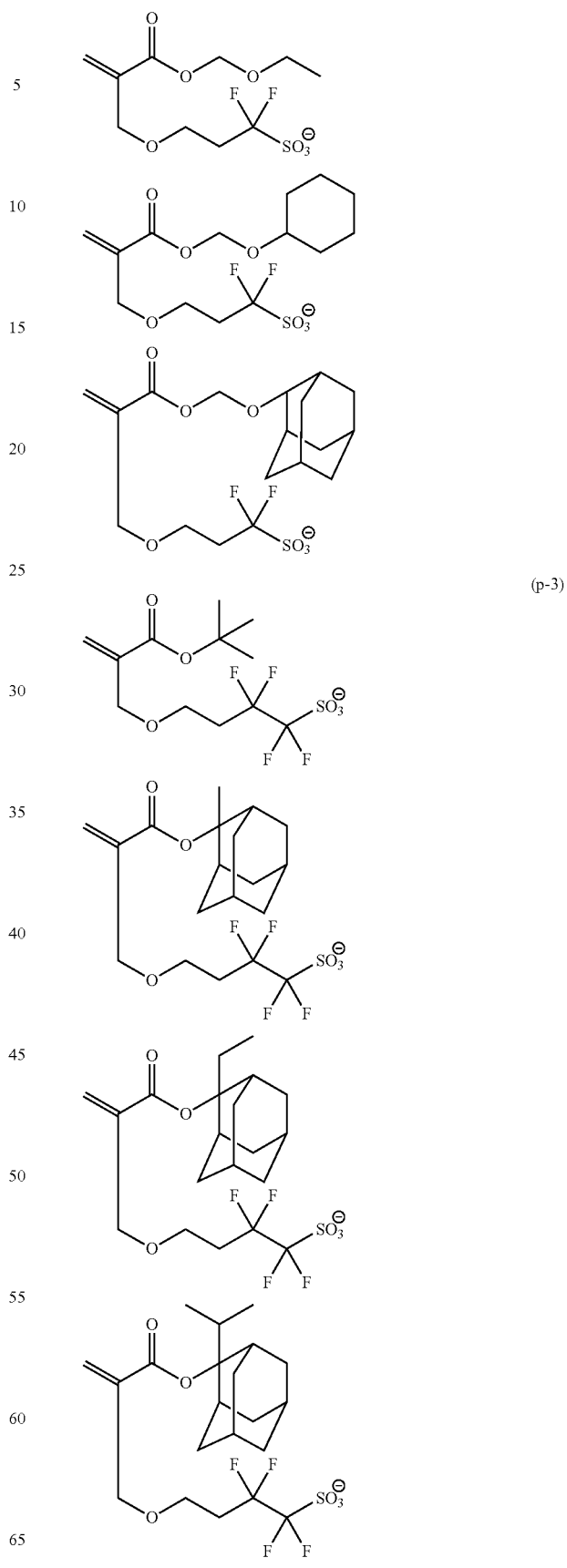
(p-3)

33
-continued
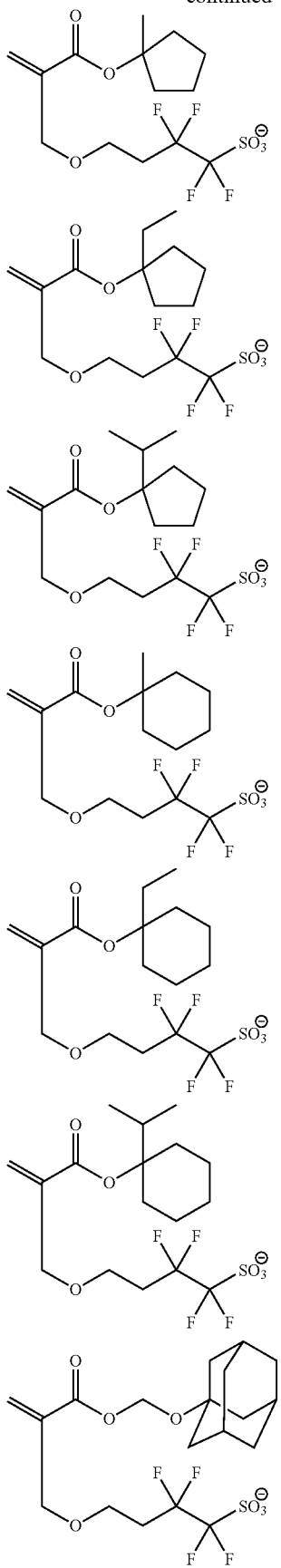
34
-continued
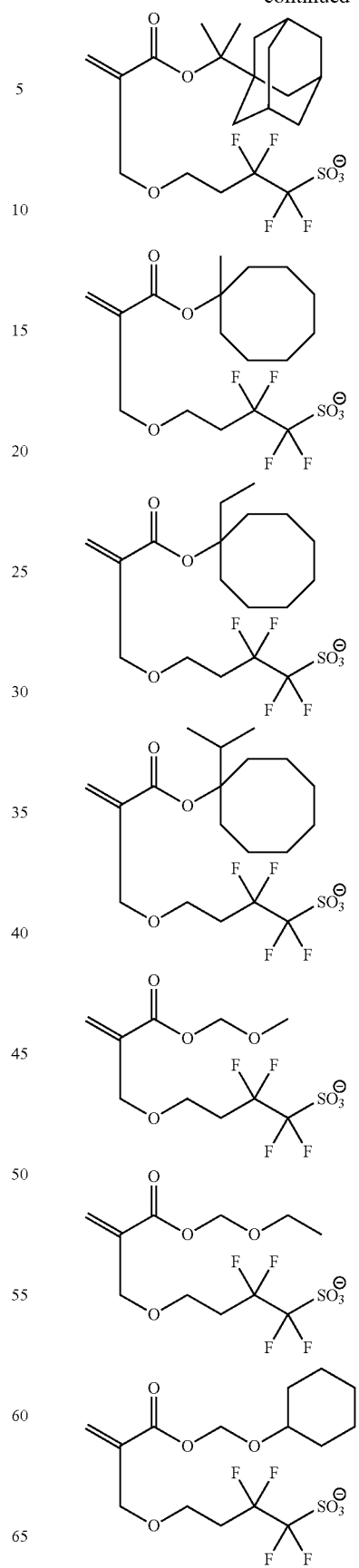

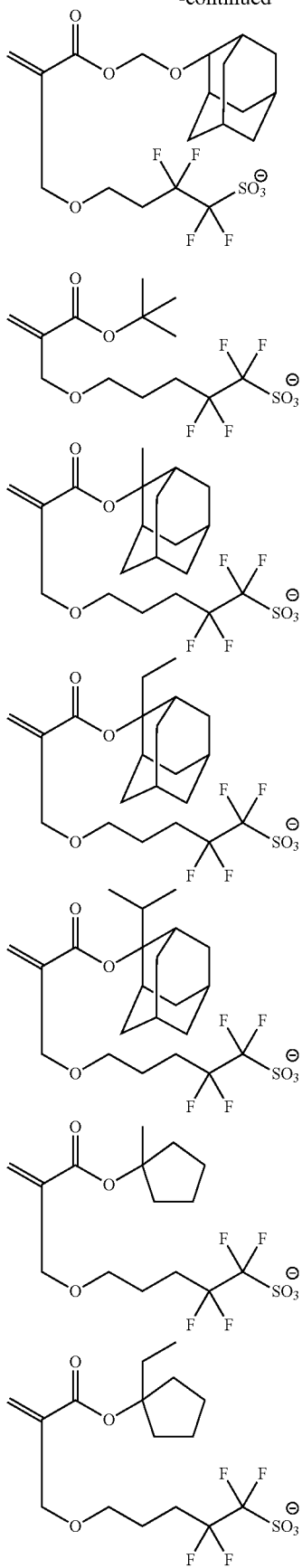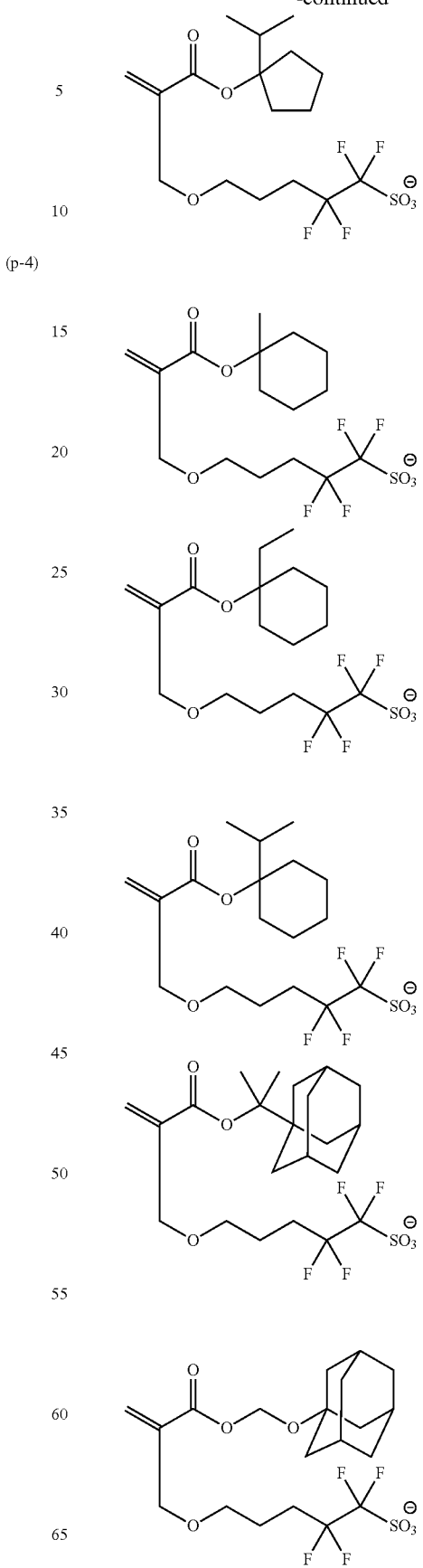
(p-4)

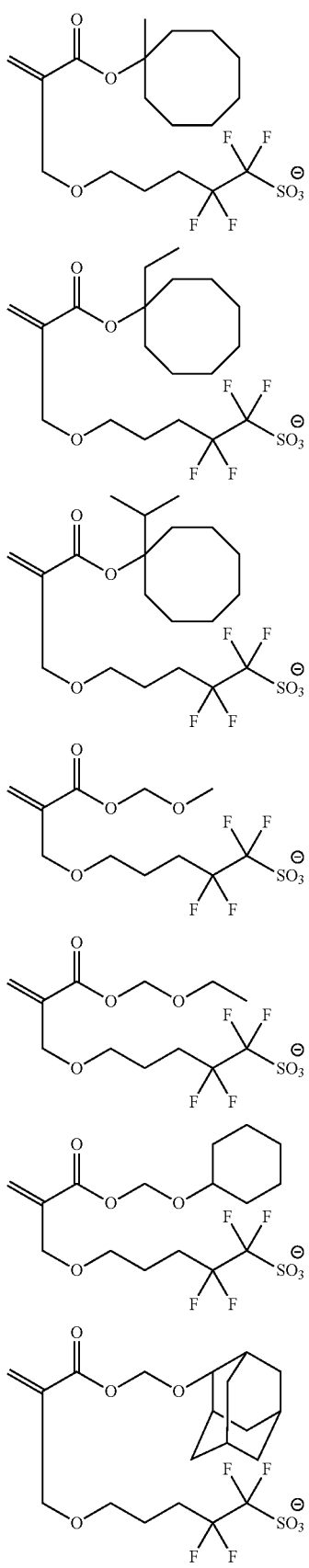
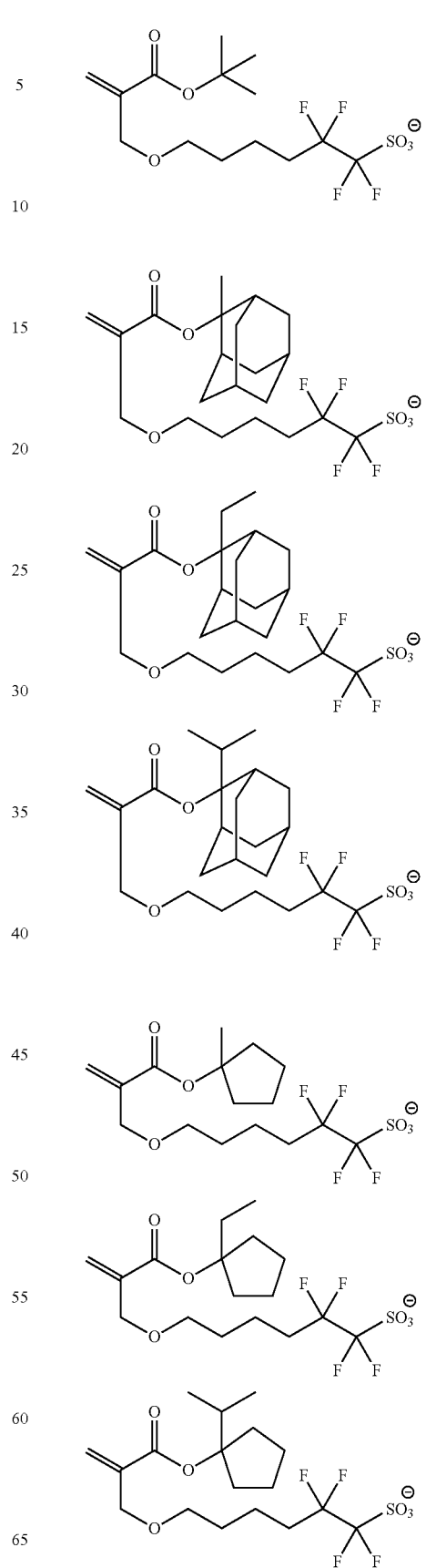
(p-5)

-continued

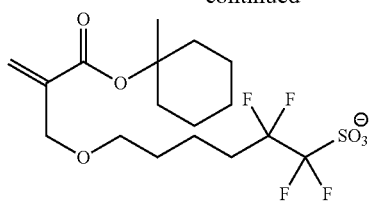
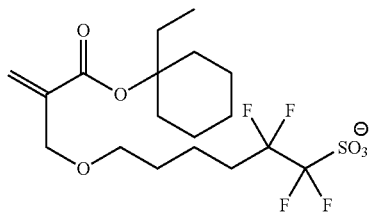
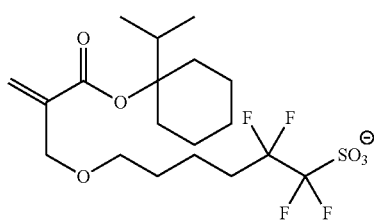
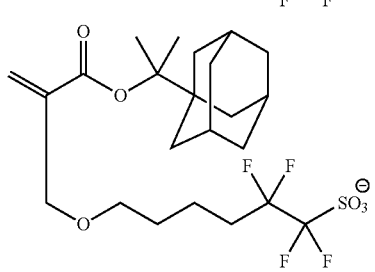
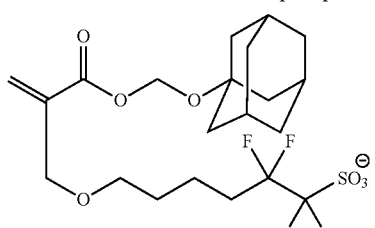
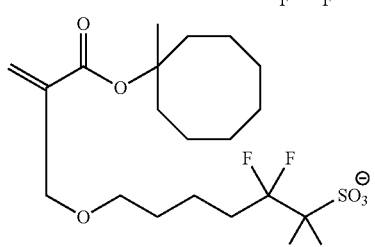
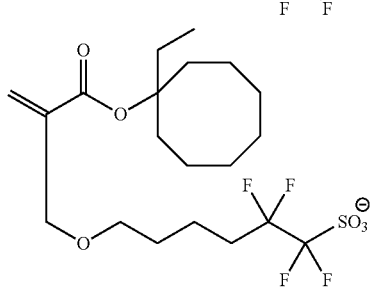

-continued

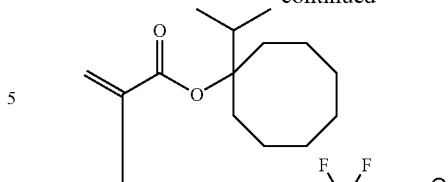
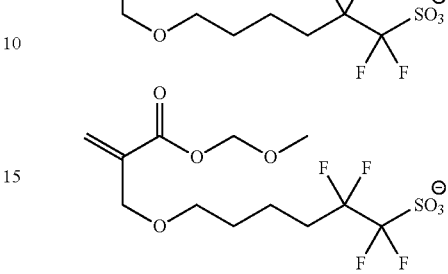
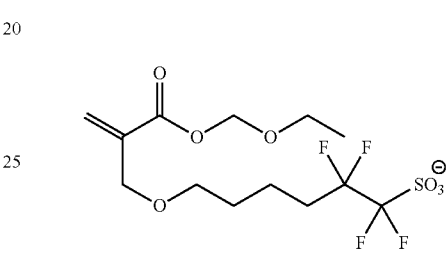
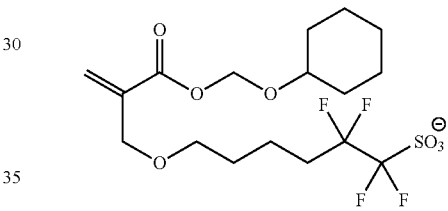
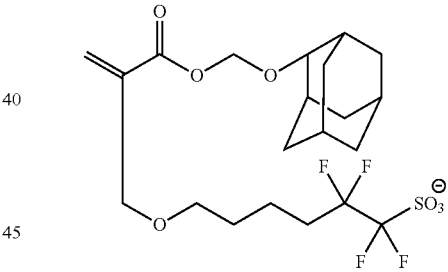

[Polymerizable Fluorine-Containing Sulfonic Acid Onium Salt]

The polymerizable fluorine-containing sulfonic acid onium salt of the general formula (2) is one preferred example of the polymerizable fluorine-containing sulfonate having the structure of the general formula (1) according to the present invention. This polymerizable fluorine-containing sulfonic acid onium salt, in the form of either a monomer or a resin obtained by homopolymerization or copolymerization thereof, is capable of sensing high energy radiation, e.g., electromagnetic wave generated by excimer laser or by synchrotron radiation, such as near-ultraviolet radiation, far-ultraviolet radiation, extreme-ultraviolet radiation (EUV), soft X-ray, X-ray or γ-ray, or charged particle beam such as electron beam, and thereby generating a fluorine-containing sulfonic acid of high acidity. The polymerizable fluorine-containing sulfonic acid onium salt or the resin obtained therefrom can be thus suitably used a photoacid generator.

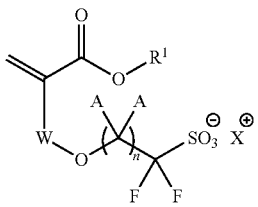

(2)

In the general formula (2), A, n, W and $R^1$ have the same definitions as in the general formula (1); and $X^+$ represents either a sulfonium cation of the following general formula (a) or a iodonium cation of the following general formula (b).

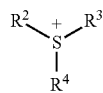

(a)

In the general formula (a), $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^{03}$, $R^{04}$ and $R^{05}$ may be bonded together to form a ring with a sulfur atom in the formula.

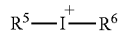

(b)

In the general formula (b), $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula.

As specific structural examples of $W^+$, the sulfonium cation of the general formula (a) and the iodonium cation of the general formula (b) will be explained below in detail.

<Sulfonium Cation of General Formula (a)>

In the general formula (a), $R^2$, $R^3$ and $R^4$ are exemplified as follows. The $C_1$-$C_{20}$ alkyl group may be straight, branched or cyclic and may be substituted or unsubstituted. Examples of the substituted or unsubstituted $C_1$-$C_{20}$ alkyl group are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl. The $C_1$-$C_{20}$ alkneyl group may be straight, branched or cyclic and may be substituted or unsubstituted. Examples of the substituted or unsubstituted $C_1$-$C_{20}$ alkenyl group are vinyl, allyl, propenyl, butenyl, hexenyl and cyclohexenyl. The $C_1$-$C_{20}$ oxoalkyl group may be straight, branched or cyclic and may be substituted or unsubstituted. Examples of the substituted or unsubstituted $C_1$-$C_{20}$ oxoalkyl group are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl. Examples of the substituted or unsubstituted $C_6$-$C_{18}$ aryl group are: phenyl; naphthyl; thienyl; alkoxylphenyl groups such as p-methoxyphenyl, m-methoxyphenyl, o-methoxyphenyl, p-ethoxypenyl, p-tert-butoxyphenyl and m-tert-butoxyphenyl; alkylphenyl groups such as 2-methylphenyl, 3-methylphenyl, 4-methylphenyl and ethylphenyl; alkylnaphthyl groups such as methylnaphthyl and ethylnaphthyl; dialkylnaphthyl groups such as diethylnaphthyl; and dialkoxynaphthyl groups such as dimethoxynaphthyl and diethoxynaphthyl. Examples of the substituted or unsubstituted $C_6$-$C_{18}$ aralkyl group are benzyl, 1-phenylethyl and 2-phenylethyl. Examples of the substituted or unsubstituted $C_6$-$C_{18}$ aryloxoalkyl group are 2-aryl-2-oxoethyl groups such as 2-phenyl-2-oxoethyl, 2-(1-naphthyl)-2-oxoethyl and 2-(2-naphthyl)-2-oxoethyl. In the case where two or more of $R^2$, $R^3$ and $R^4$ are bonded to each other to form a ring with the sulfur atom, there can be used divalent groups such as 1,4-butylene and 3-oxa-1,5-penthylene. There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general formula (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-butylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium. Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are other specific examples of the sulfonium cation of the general formula (a). There can also be used polymerizable sulfonium cations disclosed in Japanese Laid-Open Patent Publication No. 4-230645 and Japanese Laid-Open Patent Publication No. 2005-84365.

<Iodonium Cation of General Formula (b)>

Examples of $R^5$ and $R^6$ in the general formula (b) are the same as those of $R^2$, $R^3$ and $R^4$ in the general formula (a).

Specific examples of the iodonium cation of the general formula (b) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

The polymerizable fluorine-containing sulfonic acid onium salt of the general formula (2) can be exemplified by combination of the forementioned polymerizable fluorine-containing sulfonate having the structure of the general formula (1) with the sulfonium cation of the general formula (a) or the iodonium cation of the general formula (b) mentioned above. The following are particularly preferred examples of the polymerizable fluorine-containing sulfonic acid onium salt.

(q-1)

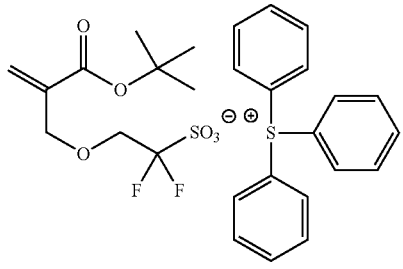

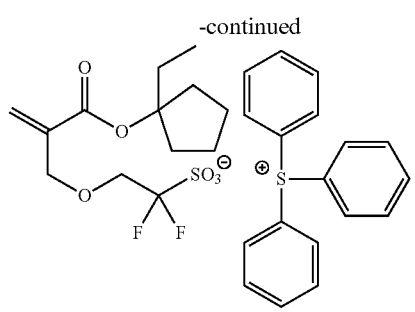

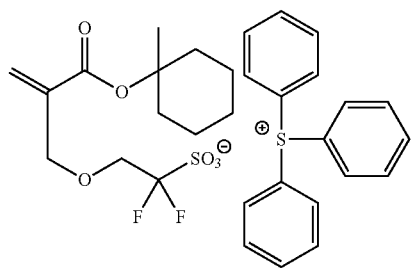

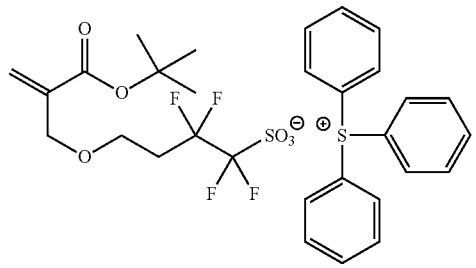

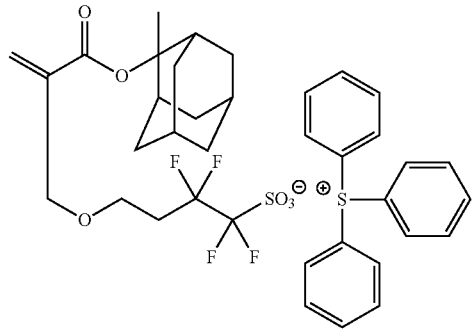

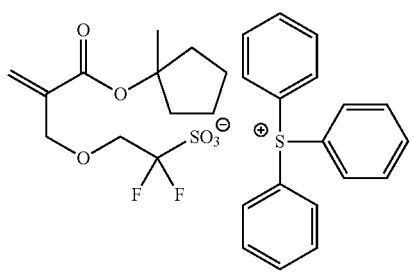

(q-2)

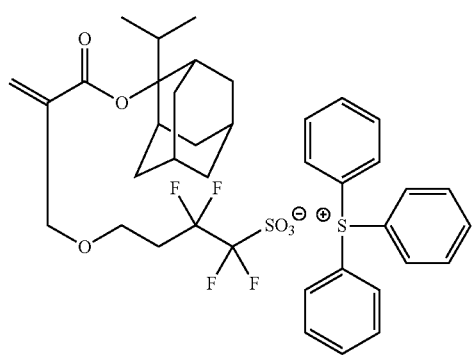

-continued

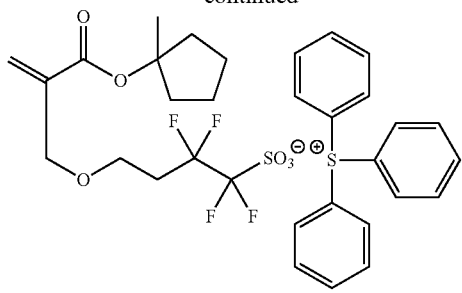

[Production Method of Polymerizable Fluorine-Containing Sulfonate]

Next, a production method of the above-mentioned polymerizable fluorine-containing sulfonate of the general formula (1) will be described below. It is feasible to produce the polymerizable fluorine-containing sulfonate of the general formula (1) in the same manner as the polymerizable fluorine-containing sulfonic acid onium salt of the general formula (2). In the following explanations, $X^+$ is readable as $M^+$.

The polymerizable fluorine-containing sulfonic acid onium salt of the general formula (2) is produced in one step from a compound of the general formula (15) and a compound of the general formula (16) as indicated in Scheme (2). It is herein noted that: this process step is merely one example and is not intended to limit the production method thereto.

Scheme (2)

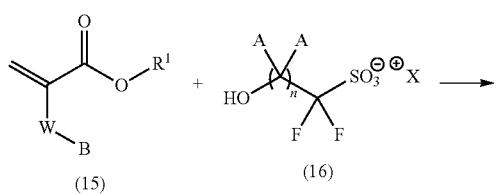

-continued

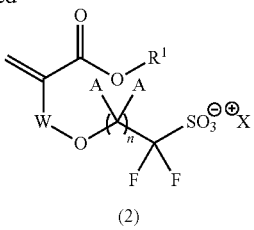

(2)

In Scheme (2), A, n, W, $R^1$ and $X^+$ have the same definitions as in the general formula (2); B represents a halogen atom or a leaving group such as hydroxy, methansulfonyloxy, 4-toluenesulfonyloxy, nitrobenzenesulfonyloxy or trifluoromethanesulfonyloxy.

The compound of the general formula (15) is an acrylic acid derivative. The acrylic acid derivative can be commercially available or can be prepared by a known process.

The compound of the general formula (16) is a hydroxyfluoroalkanesulfonic acid onium salt in which $X^+$ is either a sulfonium cation or iodonium cation. Specific examples of the cation are the same as those in the explanation of the general formula (2). There can thus be used, as the hydroxyfluoroalkanesulfonic acid onium salt, 2-hydroxy-1,1-difluoroethanesulfonic acid triphenylsulfonium, 4-hydroxy-1,1,2,2-tetrafluorobutanesulfonic acid triphenylsulfonium, 5-hydroxy-1,1,2,2-tetrafluoropentanesulfonic acid triphenylsulfonium and 6-hydroxy-1,1,2,2-tetrafluorohexanesulfonic acid triphenylsulfonium. These compounds can be produced by methods as disclosed in Japanese Laid-Open Patent Publication No. 2009-91351, International Application Publication No. WO 2008/56795, International Application Publication No. WO 2006/121096 and Japanese Laid-Open Patent Publication No. 2010-18573.

The production step involves condensation reaction of the acrylic acid derivative of the general formula (15) and the hydroxyfluoroalkanesulfonic acid onium salt of the general formula (16). The system of the condensation reaction varies depending on the kinds of W and B in the general formula (15). In either case, the condensation reaction can be performed by a general technique. The following three cases are herein exemplified below.

Case (1): where B is a halogen atom (e.g. chlorine, bromine or iodine; preferably, bromine) or a sulfonyloxy group (preferably, e.g. methanesulfonyloxy, 4-toluenesulfonyloxy, nitrobenzenesulfonyloxy or trifluoromethanesulfonyloxy); and an end of W bonded to B is alkylene (i.e. where the compound of the general formula (15) is an alkyl halide or an alkylsulfonyloxy compound).

There is no particular limitation on the amount of the alkyl halide or alkylsulfonyloxy compound of the general formula (15) reacted with the hydroxyfluoroalkanesulfonic acid onium salt of the general formula (16). The amount of the alkyl halide or alkylsulfonyloxy compound used is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

The reaction is generally performed with the use of an aprotic solvent. Examples of the aprotic solvent are dichloroethane, toluene, ethylbenzene, monochlorobenzene, acetonitrile and N,N-dimethylfoimamide. These solvents can be used solely or in combination of two or more kinds thereof.

There is no particular limitation on the reaction temperature. The reaction temperature is generally 0 to 200° C., preferably 20 to 180° C., more preferably 50 to 150° C. It is preferable to perform the reaction with stirring.

The reaction time is set depending on the reaction temperature and is generally several minutes to 100 hours, preferably 30 minutes to 50 hours, more preferably 1 to 20 hours. It is preferable to determine the time at which the hydroxyfluoroalkanesulfonic acid onium salt of the general formula (16) as the raw material has been consumed as the end of the reaction while monitoring the progress of the reaction by any analytical means such as nuclear magnetic resonance (NMR).

Further, the reaction is generally performed with the use of a base catalyst. Preferred examples of the base catalyst are: organic bases such as trimethylamine, triethylamine, tripropylamine and tributylamine; and inorganic bases such as sodium hydroxide, potassium hydroxide and lithium hydroxide. The amount of the base catalyst used is not particularly limited and is generally 0.0001 to 10 mol, preferably 0.001 to 5 mol, more preferably 0.01 to 1.5 mol, per 1 mol of the hydroxyfluoroalkanesulfonic acid onium salt of the general formula (16).

After the reaction, the polymerizable fluorine-containing sulfonic acid onium salt of the general formula (2) can be obtained by ordinary means such as extraction, crystallization or recrystallization. The polymerizable fluorine-containing sulfonic acid onium salt of the general formula (2) may be purified by recrystallization etc. as needed.

Case (2): where B is a halogen atom (e.g. chlorine, bromine or iodine; preferably, chlorine); and an end of W bonded to the halogen atom is —(C=O)— (i.e. where the compound of the general formula (15) is an acid halide).

There is no particular limitation on the amount of the acid halide of the general formula (15) reacted with the hydroxyfluoroalkanesulfonic acid onium salt of the general formula (16). The amount of the acid halide used is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

The reaction can be performed with the use of no solvent or with the use of an inert solvent. There is no particular limitation on the solvent as long as the solvent is inert to the reaction. As the hydroxyfluoroalkanesulfonic acid onium salt of the general formula (16) is almost insoluble in a nonpolar hydrocarbon solvent e.g. n-hexane, benzene or toluene, it is not preferable to use the nonpolar hydrocarbon solvent solely as the reaction solvent. Preferred examples of the inert solvent are: water; ketone solvents such as acetone, methyl ethyl ketone and methyl isobutyl ketone; ester solvents such as ethyl acetate and butyl acetate; ether solvents such as diethyl ether, diethylene glycol dimethyl ether, tetrahydrofuran and dioxane; halogenated solvents such as dichloromethane, chloroform, carbon tetrachloride, 1,2-dichloroethane, tetrachloroethylene, chlorobenzene and orthochlorobenzene; and polar solvents such as acetonitrile, N,N-dimethylformamide, N,N-imidazolidinone, dimethyl sulfoxide and sulfolane. These solvents can be used solely or in combination of two or more kinds thereof.

There is no particular limitation on the reaction temperature. The reaction temperature is generally −78 to 150° C., preferably −20 to 120° C., more preferably 0 to 100° C.

The reaction time is set depending on the reaction temperature and is generally several minutes to 100 hours, preferably 30 minutes to 50 hours, more preferably 1 to 20 hours. It is preferable to determine the time at which the hydroxyfluoroalkanesulfonic acid onium salt of the general formula (16) as the raw material has been consumed as the end of the reaction while monitoring the progress of the reaction by any analytical means such as nuclear magnetic resonance (NMR).

In the case of using the acid halide of the general formula (15), it is feasible to conduct the reaction in the presence of no catalyst while removing a hydrogen halide by-product from the reaction system or with the use of a dehydrohalogenation agent (acid acceptor). Examples of the acid acceptor are: organic bases such as triethylamine, pyridine, 1,4-diazabicyclo[2.2.2]octane (DABCO) and 1,8-diazabicyclo[5.4.0]undec-7-ene (DBU); and inorganic bases such as sodium hydrogencarbonate, sodium carbonate, potassium carbonate, lithium carbonate, sodium hydroxide, potassium hydroxide, calcium hydroxide and magnesium oxide. The amount of the acid acceptor used is not particularly limited and is generally 0.05 to 10 mol, preferably 0.1 to 5 mol, more preferably 0.5 to 3 mol, per 1 mol of the hydroxyfluoroalkanesulfonic acid onium salt of the general formula (16).

After the reaction, the polymerizable fluorine-containing sulfonic acid onium salt of the general formula (2) can be obtained by ordinary means such as extraction, crystallization or recrystallization. The polymerizable fluorine-containing sulfonic acid onium salt of the general formula (2) may be purified by recrystallization etc. as needed.

Case (3): where B is a hydroxy group (leaving group); and an end of W bonded to the hydroxy group is —(C=O)— (i.e. where the compound of the general formula (15) is a carboxylic acid).

There is no particular limitation on the amount of the carboxylic acid of the general formula (15) reacted with the hydroxyfluoroalkanesulfonic acid onium salt of the general formula (16). The amount of the carboxylic acid used is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

The reaction is generally performed with the use of an aprotic solvent. Examples of the aprotic solvent are dichloroethane, toluene, ethylbenzene, monochlorobenzene, acetonitrile and N,N-dimethylformamide. These solvents can be used solely or in combination of two or more kinds thereof.

There is no particular limitation on the reaction temperature. The reaction temperature is generally 0 to 200° C., preferably 20 to 180° C., more preferably 50 to 150° C. It is preferable to perform the reaction with stirring.

The reaction time is set depending on the reaction temperature and is generally several minutes to 100 hours, preferably 30 minutes to 50 hours, more preferably 1 to 20 hours. It is preferable to determine the time at which the hydroxyfluoroalkanesulfonic acid onium salt of the general formula (16) as the raw material has been consumed as the end of the reaction while monitoring the progress of the reaction by any analytical means such as nuclear magnetic resonance (NMR).

Further, the reaction is generally performed in the presence of an organic acid such as 4-toluenesulfonic acid and/or an inorganic acid such as sulfuric acid as an acid catalyst. The reaction may alternatively be performed with the addition of a dehydrating agent such as 1,1'-carbonyldiimidazole or N,N'-dicyclohexylcarbodiimide. The amount of the acid catalyst used is not particularly limited and is generally 0.0001 to 10 mol, 0.001 to 5 mol, 0.01 to 1.5 mol, per 1 mol of the hydroxyfluoroalkanesulfonic acid onium salt of the general formula (16).

It is preferable to conduct the esterification reaction in the presence of the acid catalyst, while removing water from the reaction system, by a Dean-Stark apparatus etc. for shortening of the reaction time. After the reaction, the polymerizable fluorine-containing sulfonic acid onium salt of the general formula (2) can be obtained by ordinary means such as extraction, crystallization or recrystallization. The polymerizable fluorine-containing sulfonic acid onium salt of the general formula (2) may be purified by recrystallization etc. as needed.

[Sulfonate Resin]

A resin having a repeating unit of the following general formula (3) (occasionally referred to as "sulfonate resin" in the present specification) is formed by cleavage of a polymerizable double bond of the polymerizable fluorine-containing sulfonate of the general formula (1-1). In the polymerization reaction, the original structure of the fluorine-containing sulfonate, other than the polymerizable double bond, is maintained with no structural changes.

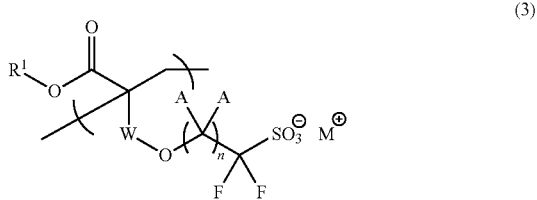

(3)

In the general formula (3), A, n, W and $R^1$ have the same definitions as in the general formula (1); and $M^+$ represents a monovalent cation.

It is preferable to use the onium cation ($X^+$) as the cation ($M^+$). In this case, a resin having a repeating unit of the following general formula (4) is formed by cleavage of a polymerizable double bond of the polymerizable fluorine-containing sulfonic acid onium salt of the general formula (2).

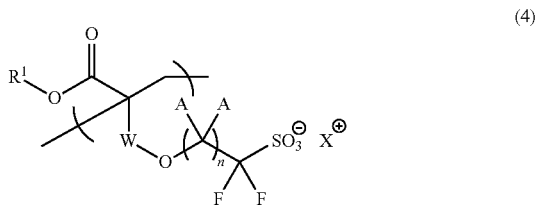

(4)

In the general formula (4), A, n, W and $R^1$ have the same definitions as in the general formula (1); and $X^+$ has the same definition as in the general formula (2).

The resin having the repeating unit of the general formula (4) is converted to the resin having the repeating unit of the general formula (5) by exposure to high energy radiation.

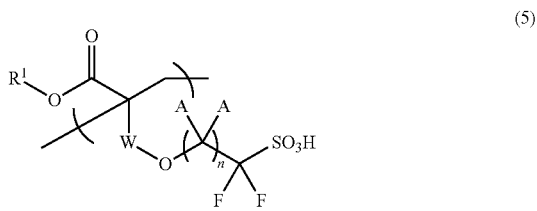

(5)

In the general formula (5), A, n, W and $R^1$ have the same definitions as in the general formula (1).

There is no particular limitation on the high energy radiation. Examples of the high energy radiation are: electromagnetic waves, such as near ultraviolet radiation, far ultraviolet radiation, extreme ultraviolet radiation (EUV), soft X-ray, X-ray and γ-ray, generated by excimer laser e.g. KrF excimer laser, ArF excimer laser or $F_2$ excimer laser or by synchrotron radiation; and charged particle beams such as electron beam. For fine patterning, it is particularly effective to use high energy radiation of 300 nm or less wavelength, such as near ultraviolet radiation, far ultraviolet radiation or extreme ultraviolet radiation (EUV) generated by excimer laser e.g. KrF excimer laser, ArF excimer laser or $F_2$ excimer laser or by synchrotron radiation.

After the elimination of the cation $X^+$, the repeating unit has a difluorosulfonic acid at an end thereof that shows very high acidity and functions as a photoacid generator for a chemically amplified resist composition. Namely, the resin having at least the repeating unit of the general formula (4) functions as a photoacid generator and performs a positive photosensitive solubility-changing function. A composition containing at least such a resin and a solvent can be thus suitably used in itself as a resist composition.

The sulfonate resin may have, in addition to the repeating unit of the general formula (4) derived from the polymerizable fluorine-containing sulfonic acid onium salt of the general formula (2), any other repeating unit (referred to as "auxiliary repeating unit" in the present specification). Herein, the term "auxiliary repeating unit" means a repeating unit that does not correspond to the repeating unit of the general formula (4); and the term "auxiliary monomer" means a monomer capable of forming an auxiliary repeating unit by cleavage of a polymerizable double bond thereof.

In other words, the sulfonate resin can be in the form of a homopolymer consisting of the repeating unit of the general formula (4) by homopolymerization of the polymerizable fluorine-containing sulfonic acid onium salt of the general formula (2) or in the form of a copolymer having not only the repeating unit of the general formula (4) but also the auxiliary repeating unit. It is feasible to use the sulfonate resin itself as a positive resist base resin or as a photoacid generator to form a resist composition in combination with another base resin.

In the case of using the sulfonate resin as the positive resist base resin, the repeating unit of the general formula (4) and the auxiliary monomer repeating unit can be included in the sulfonate resin. There is no particular limitation on the kind of the auxiliary repeating unit. It is preferable that the auxiliary repeating unit is of the type for improvement in substrate adhesion, etching resistance etc. although the auxiliary repeating unit may be of the type having a moiety capable of generating an acid by light irradiation or a moiety with an acid labile group. For such use, the sulfonate resin contains 5 to 70 mol %, preferably 10 to 60 mol %, of the repeating unit of the general formula (4) and the balance being the auxiliary repeating unit. If the amount of the repeating unit of the general formula (4) is less than 5 mol %, it becomes impossible to make sufficient use of the feature of the present invention that the resist resin combines the functions as the base resin and the photoacid generator. If the amount of the repeating unit of the general formula (4) exceeds 70 mol %, it becomes unfavorably difficult to control the properties such as substrate adhesion and etching resistance of the resist resin.

In the case of mainly using the sulfonate resin as the photoacid generator, it is generally preferable that sulfonate resin includes not only the repeating unit of the general formula (4) but also the auxiliary repeating unit although the sulfonate resin can be foamed solely of the repeating unit of the general formula (4). There is no particular limitation on the kind of the auxiliary repeating unit. It is preferable that the auxiliary repeating unit is of the type for improvement in solvent solubility, storage stability etc. although the auxiliary repeating unit may be of the type having a moiety capable of generating an acid by light irradiation or a moiety with an acid labile group. For such use, the sulfonate resin contains 5 to 100 mol %, preferably 10 to 100 mol %, of the repeating unit of the general formula (4) and the balance being the auxiliary repeating unit. If the amount of the repeating unit of the general formula (4) is less than 5 mol %, it becomes necessary to use a large amount of the sulfonate resin in order for the sulfonate resin to show sufficient sensitivity to high energy radiation as the photoacid generator in the resist composition.

In the present invention, the sulfonate resin generally has a mass-average molecular weight of 1,000 to 1,000,000, preferably 2,000 to 500,000, as measured by gel permeation chromatography (GPC). In the case of using any positive photosensitive film-forming resin in combination with the sulfonate resin, the sulfonate resin generally has a mass-average molecular weight of 1,000 to 100,000, preferably 2,000 to 50,000. If the mass-average molecular weight of the sulfonate resin is less than 1,000, a resist film formed from the resist composition deteriorates in mechanical strength. If the mass-average molecular weight of the sulfonate resin exceeds 1,000,000, the solubility of the resin in the solvent decreases so that it becomes unfavorably difficult to form a smooth resist film from the resist composition. The molecular weight distribution (Mw/Mn) of the f sulfonate resin is preferably in the range of 1.01 to 5.00, more preferably 1.01 to 4.00, still more preferably 1.01 to 3.00, most preferably 1.10 to 2.50.

As mentioned above, the sulfonate resin can be in the form of a homopolymer or a copolymer with the other monomer in the present invention. In either case, the sulfonate resin attains a photosensitive solubility-changing function for use in the positive resist composition. The other copolymerization monomer may be of the type having an acid labile group or an acid generating moiety. Various kinds of auxiliary monomers can be copolymerized in the sulfonate resin for control of dry etching resistance, standard developer compatibility, substrate adhesion, resist profile and other generally required resist performance such as resolution, heat resistance and sensitivity.

<Auxiliary Repeating Unit>

The copolymerization component (auxiliary repeating unit) will be next explained below.

In the present invention, the sulfonate resin can be produced with the use of the auxiliary monomer as the copolymerization component as mentioned above. The auxiliary monomer is preferably one or more kinds of the after-mentioned monomers for the introduction of the auxiliary repeating unit to the sulfonate resin in the present invention. Although there is no particular limitation on the auxiliary monomer, the auxiliary monomer can suitably be selected from olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. Among others, acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred as the copolymerization component.

Examples of the olefins are ethylene and propylene. Examples of the fluoroolefins are vinyl fluoride, vinylidene fluoride, trifluoroethylene, chlorotrifluoroethylene, tetrafluoroethylene, hexafluoroethylene and hexafluoroisobutene.

There is no particular limitation on the ester side chain structure of the acrylic ester or methacrylic ester. Examples of the acrylic esters or methacrylic esters are known acrylic or methacrylic ester compounds including: acrylic or methacrylic acid alkyl esters such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate and 2-hydroxypropyl acrylate or methacrylate; acrylate or methacrylate containing an ethylene glycol group, propylene glycol group or tetramethylene glycol group; acrylic or methacrylic ester containing an alkoxysilyl group; t-butyl acrylate or methacrylate; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; and acrylate or methacrylate having a ring structure such as lactone ring or norbornene ring.

There can also be used unsaturated amides such as acrylamide, methacrylamide, N-methylol acrylamide, N-methylol methacrylamide and diacetone acrylamide, acryloyl-containing compounds such as acrylonitrile and methacrylonitrile, maleic acid, fumaric acid and maleic anhydride.

Examples of the fluorine-containing acrylic esters or fluorine-containing methacrylic esters are acrylic esters or methacrylic esters each having a fluorine-containing group at α-position of the acryloyl group or the ester moiety. For instance, the monomer having a fluoroalkyl group in its α-position can suitably be exemplified by those in which a trifluoromethyl group, a trifluoroethyl group, a nonafluoro-n-butyl group etc. has been added to the α-position of the above non-fluorinated acrylic ester or methacrylic ester.

On the other hand, there can be used acrylic esters or methacrylic esters each of which has an ester moiety with a fluorine-containing group. In this case, the fluorine-containing group is a perfluoroalkyl group, a fluoroalkyl group or a fluorine-containing cyclic group having a fluorine atom or trifluoromethyl group as a substitutent on its ring atom, such as a fluorine-containing benzene ring, a fluorine-containing cyclopentane ring, a fluorine-containing cyclohexane ring or a fluorine-containing cycloheptane ring. Typical examples of such fluorine-containing acrylic esters or methacrylic esters are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate and perfluorocyclohexylmethyl methacrylate. There can also be used acrylic esters or methacrylic esters whose ester moiety is a fluorine-containing t-butyl ester group.

Further, a cyano group may be bonded to α-position in the above acrylic esters or fluorine-containing esters.

As the norbornene compounds and fluorine-containing norbornene compounds, norbornene monomers having a mononuclear or multinuclear structure can be used without particular limitation. Suitable examples of the norbornene compounds are those each formed by Diels-Alder addition reaction of an unsaturated compound such as an allyl alcohol, a fluorine-containing allyl alcohol, an acrylic acid, an α-fluoroacrylic acid, a methacrylic acid or any of the acrylic esters, methacrylic esters, fluorine-containing acrylic esters and fluorine-containing methacrylic esters described in the present specification with cyclopentadiene or cyclohexadiene.

The styrenic compounds, fluorine-containing styrenic compounds, vinyl ethers, fluorine-containing vinyl ethers, allyl ethers, vinyl esters, vinyl silanes and the like are also usable. Examples of the styrenic compounds and fluorine-containing styrenic compounds are styrene, fluorinated styrene, hydroxystyrene, styrenic compounds in which hexafluoroacetone has been added to the benzene ring and compounds obtained by substitution of a hydrogen atom or atoms on the benzene ring of the styrene or hydroxystyrene with a trifluoromethyl group. A halogen atom, an alkyl group or a fluorine-containing alkyl group may be bonded to α-position of the above styrenic compounds or fluorine-containing styrenic compounds. Examples of the vinyl ethers and fluorine-containing vinyl ethers are: alkyl vinyl ethers having an alkyl group such as methyl or methyl or a hydroxyalkyl group such as hydroxyethyl or hydroxybutyl, in which a part or all of hydrogen atoms may be substituted with a fluorine atom; cyclic vinyl ethers such as cyclohexyl vinyl ether and those each containing an oxygen atom or carbonyl bond in its cyclic structure; and monomer compounds each obtained by substitution of a part or all of hydrogen atoms of the above cyclic vinyl ethers with a fluorine atom. As the allyl ethers, vinyl esters and vinyl silane, there can be used known compounds without particular limitation.

One preferred example of the auxiliary repeating unit is a repeating unit of the following general formula (8).

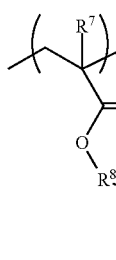

(8)

In the general formula (8), $R^7$ represents a hydrogen atom, a halogen atom or a $C_1$-$C_3$ alkyl or fluorine-containing alkyl group; $R^8$ represents a substituted or unsubstituted aliphatic hydrocarbon group, a substituted or unsubstituted divalent aromatic group or a divalent organic group formed by combination of a plurality thereof, in which any number of hydrogen atoms may be substituted with a fluorine atom; $R^9$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, in which any number of hydrogen atoms may be substituted with a fluorine atom, and may contain an ether bond or a carbonyl group; and s represents an integer of 2 to 8.

Examples of the halogen atom as $R^7$ are fluorine, chlorine and bromine. Examples of the $C_1$-$C_3$ alkyl group as $R^7$ are methyl, ethyl, propyl and isopropyl. Examples of the $C_1$-$C_3$ fluorine-containing alkyl group as $R^7$ are those obtained by substitution of a part or all of hydrogen atoms of the above alkyl group with a fluorine atom, such as trifluoromethyl, trifluoroethyl, 1,1,1,3,3,3-hexafluoroisopropyl and heptafluoroisopropyl. Among others, preferred are a hydrogen atom, a fluorine atom, a methyl group and a trifluoromethyl group. As mentioned above, $R^8$ is a substituted or unsubstituted aliphatic hydrocarbon group, a substituted or unsubstituted aromatic group or an organic group formed by combination of a plurality of substituted or unsubstituted aliphatic hydrocarbon and/or aromatic groups. Any number of hydrogen atoms of $R^8$ may be substituted with a fluorine atom. The unsubstituted aliphatic hydrocarbon group may be straight, branched or cyclic. Examples of the divalent aliphatic hydrocarbon group as $R^8$ are: straight or branched aliphatic hydrocarbon groups such as methylene, ethylene, isopropylene and t-butylene; and cyclic aliphatic hydrocarbon groups such as cyclobutylene, cyclohexylene, divalent norbornene and divalent adamantane. Examples of the unsubstituted aromatic group as $R^8$ are divalent aromatic groups such as phenylene and naphthylene. In each of the above unsubstituted aliphatic hydrocarbon and aromatic groups, any number of hydrogen atoms may be substituted with a substituent. The substituent is not particularly limited and is preferably a halogen atom (notably, fluorine atom), an alkyl group, a fluorine-containing alkyl group (notably, trifluoromethyl group or perfluoroethyl group) or the like.

As preferred examples of the repeating unit of the general formula (8), repeating units of the following general formulas (9) to (11) are exemplified.

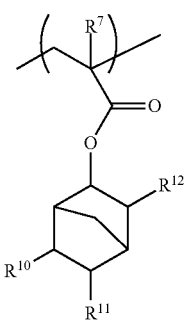

(9)

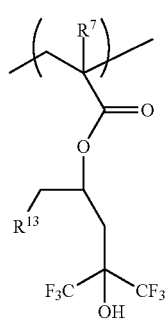

(10)

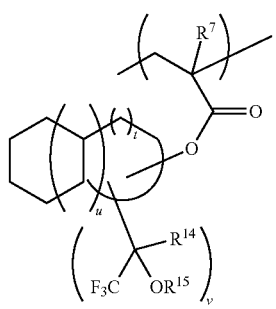

(11)

In the general formula (9), $R^7$ has the same definition as in the general formula (8); one of $R^{10}$, $R^{11}$ and $R^{12}$ represents a $CF_3C(CF_3)(OH)CH_2$ group; and the other two of $R^{10}$, $R^{11}$ and $R^{12}$ each represent a hydrogen atom.

In the general formula (10), $R^7$ has the same definition as in the general formula (8); and $R^{13}$ represents a hydrogen atom or a $C_1$-$C_4$ alkyl or fluorine-containing alkyl group. Examples of the $C_1$-$C_4$ alkyl or fluorine-containing alkyl group are methyl, ethyl, n-propyl, isopropyl, n-butyl, sec-butyl, tert-butyl, fluoromethyl, difluoromethyl, trifluoromethyl and perfluoroethyl.

In the general formula (11), $R^7$ has the same definition as in the general formula (8); $R^{14}$ represents a methyl group or a trifluoromethyl group; $R^{15}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an oxygen atom (ether bond) or a carbonyl group; u represents an integer of 0 to 2; t and v represent an integer of 1 to 8 and satisfy a relationship of $v \leq t+2$; and, in the case where each of $R^{14}$ and $R^{15}$ is present in a plural number, plural $R^{14}$, $R^{15}$ may be the same or different.

Examples of the substituted or unsubstituted $C_1$-$C_{25}$ aliphatic hydrocarbon group or substituted or unsubstituted $C_1$-$C_{25}$ aromatic hydrocarbon group as $R^{15}$ in the general formula (11) are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, in each of which a part or all of hydrogen atoms may be substituted with a fluorine atom. Oxygen-containing hydrocarbon groups such as an alkoxycarbonyl group, an acetal group and an acyl group can also be used. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above groups may be substituted with fluorine.

As the auxiliary repeating unit, a repeating unit of the following general formula (12) can suitably be used in combination with the repeating unit of the general formula (4).

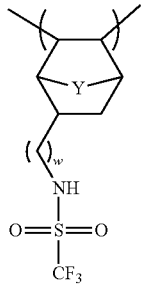

(12)

In the general formula (12), Y represents either —$CH_2$—, —O— or —S—; and w represents an integer of 2 to 6.

A repeating unit of the following general formula (13) can also suitably be used in combination with the repeating unit of the general formula (4).

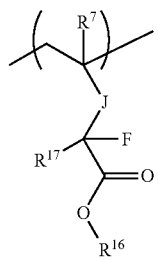

(13)

In the general formula (13), $R^7$ has the same definition as in the general formula (8); $R^{17}$ represents a hydrogen atom, a fluorine atom or a fluorine-containing alkyl group; $R^{16}$ corresponds in definition to $R^{15}$ in the general formula (11); J represents a divalent linking group and corresponds in definition to the above-mentioned linking group W; $R^{17}$ represents a hydrogen atom, a fluorine atom or a fluorine-containing alkyl group. There is no particular limitation on the fluorine-containing alkyl group. Examples of the fluorine-containing alkyl group are those of 1 to 12 carbon atoms, preferably 1 to 3 carbon atoms, such as trifluoromethyl, pentafluoroethyl, 2,2,2-trifluoroehyl, n-heptafluoropropyl, 2,2,3,3,3-pentafluoropropyl, 3,3,3-trifluoropropyl and hexafluoroisopropyl. A fluorine atom or a trifluoromethyl group is preferred as $R^{17}$.

Further, a repeating unit of the following general formula (14) can suitably be used in combination with the repeating unit of the general formula (4).

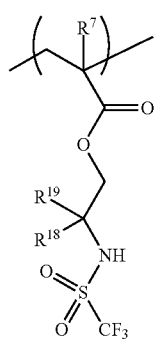

(14)

In the general formula (14), $R^7$ has the same definition as in the general formula (8); $R^{18}$ and $R^{19}$ each independently represent a hydrogen atom, a substituted or unsubstituted $C_1$-$C_{25}$ straight, branched or cyclic aliphatic hydrocarbon group or a substituted or unsubstituted $C_1$-$C_{25}$ aromatic hydrocarbon group, in which any number of hydrogen atoms may be substituted with a fluorine atom; and each of $R^{18}$ and $R^{19}$ may contain an ether bond or a carbonyl group. Examples of $R^{18}$, $R^{19}$ are the same as those of $R^{15}$ in the general formula (11).

<Auxiliary Repeating Unit with Photoacid Generating Function>

The copolymerization component (auxiliary repeating unit) with the photoacid generating function will be explained below.

As mentioned above, it is feasible to copolymerize the monomer (polymerizable compound) having the photoacid generating function with the polymerizable fluorine-containing sulfonic acid onium salt monomer although the polymerizable fluorine-containing sulfonic acid onium salt monomer itself performs the function of the photoacid generator in the present invention. As such a copolymerization monomer, there can be used any of the above-mentioned olefins, fluorine-containing olefins, acrylic acid esters, methacrylic acid esters, fluorine-containing acrylic acid esters, fluorine-containing methacrylic acid esters, norbornene compounds, fluorine-containing norbornene compounds, styrenic compounds, fluorine-containing styrenic compounds, vinyl ethers and fluorine-containing vinyl ethers having, in the molecule, a moiety capable of generating an acid by light irradiation (moiety with photoacid generating function).

The moiety capable of generating the acid by light irradiation may have a structure known as an acid generating moiety of any photoacid generator conventionally used in a chemically amplified resist material. Example of the acid generating moiety are a sulfonic acid onium salt moiety, a carboxylic acid onium salt moiety, a sulfone-amide acid onium salt moiety and a carbolic acid onium salt moiety.

Among others, a repeating unit having a sulfonic acid onium salt moiety of the following general formula (6) is particularly preferred.

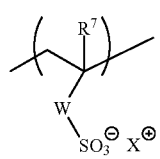
(6)

In the general formula (6), $R^7$ represents a hydrogen atom, a halogen atom or a $C_1$-$C_3$ alkyl or fluorine-containing alkyl group; W has the same definition as in the general formula (1); and $X^+$ has the same definition as in the general formula (2).

Specific examples of W are the same as those in the explanation of the general formula (1). Specific examples of $X^+$ are the same as those in the explanation of the general formula (2).

The following are specific examples of the anion structure.

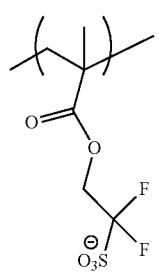
(r)

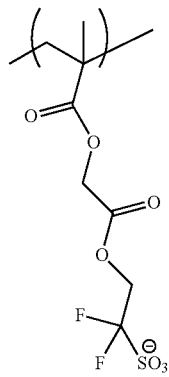

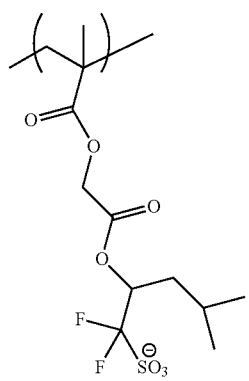

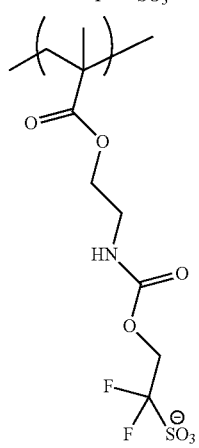

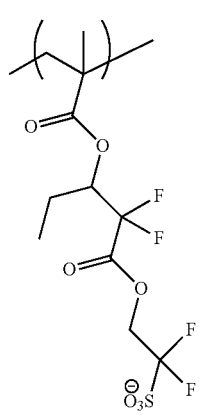

-continued

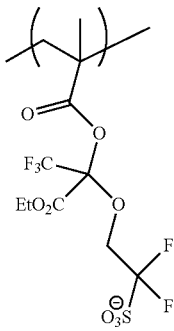

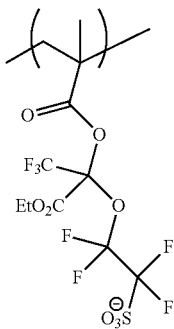

In the case where the sulfonate resin contains the repeating unit formed by cleavage of the polymerizable double bond of the monomer having the photoacid generating function, the content amount of this repeating unit is 0 to 90 mol %, preferably 2 to 80 mol %, more preferably 5 to 70 mol %, based on the total amount of the auxiliary repeating units. This repeating unit is not necessarily contained in the sulfonate resin. If the content amount of this repeating unit exceeds 90 mol %, the range of adjustment of the resist performance such as substrate adhesion and resist durability by the auxiliary repeating units becomes narrowed so that there arises a difficulty in the design of the resist resin.

<Auxiliary Repeating Unit with Acid Labile Group>

The copolymerization monomer (auxiliary repeating unit) with the acid labile group will be explained below.

As mentioned above, it is feasible to copolymerize the monomer having the acid labile group with the polymerizable fluorine-containing sulfonic acid onium salt monomer although the polymerizable fluorine-containing sulfonic acid onium salt monomer itself performs the function of the photoacid generator and has the capability of changing developer solubility by the action of the acid in the present invention. As such a copolymerization monomer, there can be used any of the above-mentioned olefins, fluorine-containing olefins, acrylic acid esters, methacrylic acid esters, fluorine-containing acrylic acid esters, fluorine-containing methacrylic acid esters, norbornene compounds, fluorine-containing norbornene compounds, styrenic compounds, fluorine-containing styrenic compounds, vinyl ethers and fluorine-containing vinyl ethers having, in the molecule, a moiety capable of being dissociated by the action of an acid (moiety with acid labile group).

Among others, a repeating unit of the following general formula (7) is particularly preferred.

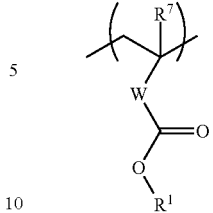

(7)

In the general formula (7), W and $R^1$ have the same definitions as in the general formula (1); and $R^7$ has the same definition as in the general formula (6). Specific examples of W and $R^1$ are the same as those in the explanation of the general formula (1).

In the case where the sulfonate resin contains the repeating unit formed by cleavage of the polymerizable double bond of the monomer having the acid labile group, the content amount of this repeating unit is 0 to 99 mol %, preferably 15 to 80 mol %, more preferably 25 to 70 mol %, based on the total amount of the auxiliary repeating units. This repeating unit is not necessarily contained in the sulfonate resin. If the content amount of this repeating unit exceeds 90 mol %, the range of adjustment of the resist performance such as substrate adhesion and resist durability by the auxiliary repeating units becomes narrowed so that there arises a difficulty in the design of the resist resin.

<Polymerization Process>

A polymerization process for production of the sulfonate resin having the repeating unit of the general formula (4) will be next explained below.

In the present invention, there is no particular limitation on the polymerization process for production of the resin having the repeating unit of the general formula (4). It is preferable to adopt radical polymerization process or ionic polymerization process. In some cases, it is feasible to adopt coordination anionic polymerization process, living anionic polymerization process, cationic polymerization process, ring opening metathesis polymerization process, vinylene polymerization process or vinyl addition process. Any common polymerization technique is applicable in each of these polymerization processes.

In the radical polymerization process, the polymerization reaction can be performed by a known polymerization technique such as bulk polymerization, solution polymerization, suspension polymerization or emulsion polymerization technique in a batch, semi-continuous or continuous system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction.

Further, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents can also be used. These solvents can be used solely or in combination of two or more thereof A molecular weight adjusting agent such as mercaptan may be used in combination.

The reaction temperature of the copolymerization reaction is set as appropriate depending on the kind of the radical polymerization initiator or radical initiating source and is generally preferably in the range of 20 to 200° C., more preferably 30 to 140° C.

As a technique for removing water or the organic solvent from the resulting fluorine-containing polymer solution or dispersion, it is feasible to adopt reprecipitation, filtration, distillation by heating under reduced pressure or the like.

[Resist Composition]

A resist composition will be next explained below.

In the present invention, the resin having the repeating unit of the general formula (4) can be used in the resist composition in the form of a solution mixed with other components. As the sulfonate resin functions as the photoacid generator and as the positive resist base resin, it is feasible to prepare the chemically amplified resist composition from the sulfonate resin without separately adding any resin (base resin) having a repeating unit with an acid labile group. The resist composition may alternatively be prepared by the addition of a resin having a repeating unit with an acid labile group. The resist composition includes a solvent and optionally various additives commonly used for resist compositions, such as an additive resin, a quencher, a dissolution inhibitor, a plasticizer, a stabilizer, a coloring agent, a surfactant, a viscosity improver, a leveling agent, an antifoaming agent, a compatibilizer, a primer and an antioxidant. As these additives, there can suitably be used any known additives in addition to the following compounds.

<Base Resin>

In the present specification, the base resin refers to a resin containing an acid labile group. Thus, the sulfonate resin having the repeating unit of the general formula (4) is one type of base resin.

Examples of the base resin for use in the positive resist composition are those each containing a leaving site such as carboxyl group or hydroxy group protected by an acid labile group on a side chain and having a main chain formed by cleavage of a polymerizable double bond of acrylic acid, methacrylic acid, α-trifloromethylacrylic acid, vinyl group, allyl group, norbornene group or the like.

In many cases, the base resin is in copolymer form for control of the resist performance. Herein, the above explanations of the copolymerization component, the acid labile group and the linking group (W) between the main chain and the acid labile group can be applied as they are to the base resin. As the copolymerization component of the base resin, a lactone ring-containing monomer is particularly preferred for improvement in the substrate adhesion of the resist composition. A hydroxyl-containing monomer is also preferred for improvement in resist solvent solubility.

The base resin generally has a mass-average molecular weight of 1,000 to 1,000,000, preferably 2,000 to 500,000, as measured by gel permeation chromatography (GPC). If the mass-average molecular weight of the base resin is less than 1,000, the resulting resist composition is not formed into a film with sufficient strength. If the mass-average molecular weight of the base resin exceeds 1,000,000, the solubility of the base resin in the solvent becomes lowered so that it becomes unfavorably difficult to form the resist composition into a smooth film. The molecular weight distribution (Mw/Mn) of the base resin is preferably in the range of 1.01 to 5.00, more preferably 1.01 to 4.00, still more preferably 1.01 to 3.00, most preferably 1.10 to 2.50.

<Additives>

The additives will be explained below.

The basic compound is preferably contained in the resist composition so as to function as a quencher or to obtain improvements in resist pattern shape, post exposure stability and the like in the present invention.

There can be used any known basic compounds such as primary, secondary and tertiary aliphatic amines, aromatic amines, heterocyclic amines, nitrogen-containing compounds with hydroxyphenyl group, alcoholic nitrogen-containing compounds and amide derivatives. Among others, secondary and tertiary aliphatic amines, aromatic amines and heterocyclic amines are preferred.

The aliphatic amines can be an alkylamine or alkylalcoholamine obtained by replacing at least one hydrogen atom of ammonia ($NH_3$) with a $C_1$-$C_{12}$ alkyl or hydroxyalkyl group. Examples of the aliphatic amine are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines such as aniline, aniline derivatives, e.g., N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines, e.g., bis(1,2,2,6,6-pentamethyl-4-piperidyl)sebacate; and alcoholic nitrogen-containing compounds such as 2-hydroxypyridine, aminocresol, 2,4-quinolinediol, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine. The above basic compounds can be used solely or in combination of two or more thereof.

The amount of the basic compound used is generally 0.01 to 5 parts by mass per 100 parts by mass of the base resin.

<Solvent>

One method of forming the sulfonate resin into a thin film is to dissolve the resin etc. in an organic solvent, and then, apply and dry the resulting resin solution.

There is no particular limitation on the organic solvent as long as the fluorine-containing polymer compound can be dissolved in the organic solvent. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof.

<Surfactant>

The surfactant, preferably either one or two or more of fluorine- and/or silicon-based surfactants (fluorine-based surfactant, silicon-based surfactants, surfactant containing both of fluorine and silicon atoms) is contained in the resist composition in the present invention.

The addition of such a surfactant into the resist composition is effective for use with an exposure light source of 250 nm or less wavelength, notably 220 nm or less wavelength, and for pattern formation with a narrower pattern line width so that the resist composition can attain good sensitivity and resolution and allow good resist patterning with less adhesion/development failures.

<Acid Generator>

In the present invention, there can be used a known photoacid generator in combination with the sulfonate resin although there is no need to add a photoacid generator separately to the resist composition.

As the photoacid generator, it is feasible to select and use any one of ordinary photoacid generators of chemically amplified resist compositions. Examples of the photoacid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The amount of the photoacid generator used is generally in the range of 0 to 30 parts by mass, preferably 0 to 20 parts by mass, per 100 parts by mass of the sum of the sulfonate resin and the other base resin. If the amount of the photoacid generator exceeds 30 parts by mass, it becomes difficult to prepare the resin composition as a uniform solution. Further, the resin composition unfavorably tends to become low in storage stability.

<Additive Resin>

There is no particular limitation on the additive resin as long as the additive resin can be dissolved in the solvent used and has compatibility with the other components of the resist composition. The additive resin functions as a plasticizer, a stabilizer, a viscosity improver, a leveling agent, an antifoaming agent, a compatibilizer, a primer etc.

[Pattern Formation Method]

A pattern formation method will be explained below. In the present invention, the resist composition can be used for resist pattern formation by a conventional photoresist technique.

For example, the resist composition is first prepared in solution form, applied to a substrate such as a silicon wafer by e.g. a spinner, and then, dried. The resulting photosensitive film is irradiated with high energy radiation or electron beam by an exposure device etc. through a desired mask pattern and subjected to heating. Subsequently, the photosensitive film is developed with an aqueous alkaline developer such as aqueous solution of 0.1 to 1 mass % tetramethylammoniumhydroxide. It is possible by the above method to form a resist pattern according to the mask pattern. As mentioned above, various additives compatible with the resist composition, such as additive resin, quencher, plasticizer, stabilizer, coloring agent, surfactant, viscosity improver, leveling agent, antifoaming agent, compatibilizer, primer and antioxidant can be added as desired.

There is no particular limitation on the high energy ray radiation used in the present invention. For fine patterning, high energy radiation of 300 nm or less wavelength, such as electromagnetic wave e.g. near-ultraviolet radiation (wavelength: 380 to 200 nm), vacuum ultraviolet radiation (far-ultraviolet radiation, VUV, wavelength: 200 to 10 nm), extreme ultraviolet radiation (EUV, wavelength: 10 nm or less), soft X-ray, X-ray or γ-ray generated by F2 excimer laser, ArF excimer laser, KrF excimer laser or synchrotron radiation, or electron beam radiation is particularly effective. It is herein noted that: the designation of the electromagnetic wave radiation is for convenience; and the physical/chemical action of the electromagnetic wave radiation naturally depends on the radiation wavelength. The exposure can preferably be carried out with soft X-ray radiation of 10 to 14 nm wavelength. It is effective to adopt the exposure device with the radiation source of such short-wavelength high energy radiation or electron beam radiation of 300 nm or less wavelength. The resist composition can also be applied suitably and effectively to a liquid immersion exposure device, which uses a medium causing less absorption of high energy radiation, such as water or fluorinated solvent, in a part of optical path and enables more efficient fine processing in terms of numerical aperture and effective wavelength.

For example, it is feasible to carry out the exposure by liquid immersion lithography, with the use of the liquid immersion exposure device, in which water or any liquid medium other than water, having a higher refractive index than air, is inserted between the substrate to which the resist composition has been applied and a projection lens.

EXAMPLES

Hereinafter, the present invention will be described in more detail below by way of the following synthesis examples, working examples and comparative examples. It should be noted that the following working examples are illustrative and are not intended to limit the present invention thereto.

Synthesis Example 1

2-[2-(t-Butoxycarbonyl)allyloxy]-1,1-difluoroethanesulfonic acid triphenylsulfonium

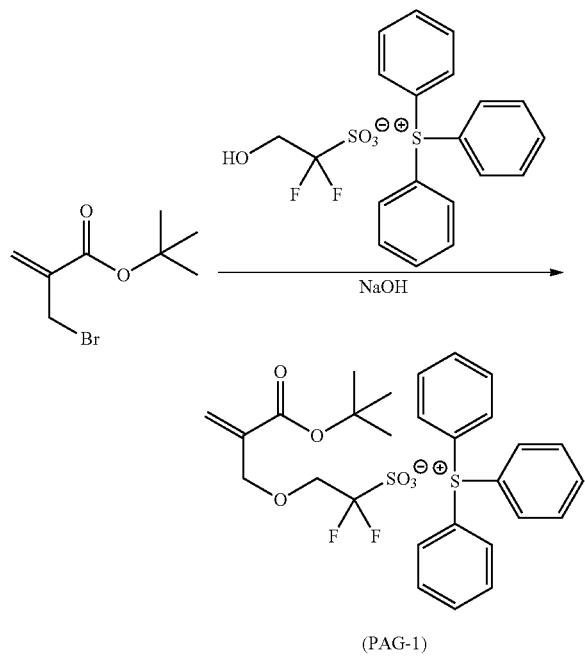

(PAG-1)

Synthesis of Target Compound (PAG-1)

In a 100-ml flask, 31 g of an aqueous solution of 5 mass % sodium hydroxide was placed. The solution was cooled, with stirring, by immersing the flask in an ice water bath. Then, 15.0 g of 2-hydroxy-1,1-difluoroethanesulfonic acid triphenylsulfonium (purity: 95%, 0.035 mol) was gradually added to the solution. The solution was returned to room temperature and stirred for 30 minutes. The solution was again cooled by immersing the flask in the ice water bath. After that, a solution of 6.5 g of tert-butyl 2-bromomethylacrylate (0.029 mol) in 10 g of acetonitrile was dropped into the above solution. The mixed solution was further stirred for 1.5 hours at room temperature. The thus-obtained reaction solution was separated into upper and lower layers. The lower layer was mixed with 20 g of chloroform and washed three times with 24 g of water. The resulting solution was solidified by concentration under reduced pressure. The solid product was dissolved in 10 g of methyl ethyl ketone at 40° C. Into the product solution, 25 g of diisopropyl ether was slowly dropped. The product solution was then stirred for 1 hour at room temperature. After confirming the deposition of a crystalline substance, the crystalline substance was filtered out and dried under reduced pressure. With this, 10 g of the target compound (PAG-1) was obtained as a white solid substance (purity: 99%, yield: 88%).

<Properties of Target Compound (PAG-1)>

$^1$H NMR (measurement solvent: deuterated chloroform, reference material: tetramethylsilane): δ=7.70-7.60 (m, 15H), 6.10 (s, 1H), 5.74 (s, 1H), 4.25 (s, 2H), 4.14 (t, 2H), 1.39 (s, 9H).

$^{19}$F NMR (measurement solvent: deuterated chloroform, reference material: trichlorofluoromethane): δ=−114.66 (t, 2F).

Synthesis Example 2

2-[2-(2-Methyladamantaneoxycarbonyl)allyloxy]-1,1-difluoroethanesulfonic acid triphenylsulfonium

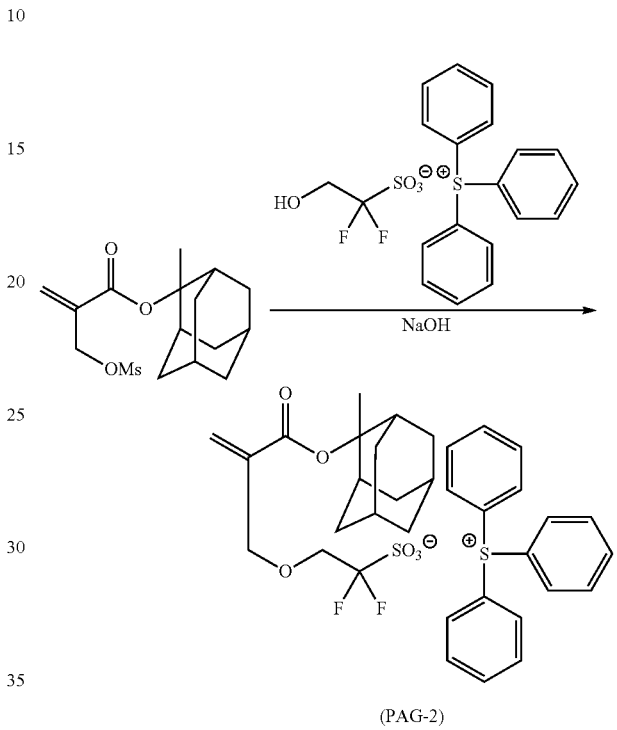

(PAG-2)

Synthesis of Target Compound (PAG-2)

In a 500-ml three-neck flask, 39.8 g (45.6 mmol) of an aqueous solution of 5% sodium hydroxide and 16.1 g (38.0 mmol) of 2-hydroxy-1,1-difluoroethanesulfonic acid triphenylsulfonium were placed. The resulting solution was stirred for 10 minutes at room temperature, thereby completely dissolving the solid substance. Subsequently, 25 g of crude 2-methyladamantyl 2-[(methanesulfonyloxy)methyl]acrylate was dropped and mixed into the solution. The mixed solution was then stirred for 1 hour at room temperature. After the completion of the reaction, the thus-obtained reaction solution was separated into an aqueous layer and a target product layer. The aqueous layer was extracted with 45 g of chloroform. The target product layer was combined with the chloroform extract. The combined product layer was washed five times with 45 g of water, washed twice with 30 g of 0.1N hydrochloric acid and further washed twice with 45 g of water. The washed product layer was concentrated under reduced pressure to distill therefrom a major part of the organic solvent. The resulting product was purified by column chromatography and dissolved in 10 g of methyl ethyl ketone at 40° C. Into the product solution, 30 g of diisopropyl ether was slowly dropped. The product solution was stirred for 1 hour at room temperature. After confirming the deposition of a crystalline substance, the crystalline substance was filtered out and dried under reduced pressure. With this, 10.5 g of the target compound (PAG-2) was obtained as a white solid substance (purity: 96%, yield: 28%).

<Properties of Target Compound (PAG-2)>

$^1$H NMR (measurement solvent: deuterated chloroform, reference material: tetramethylsilane): δ=7.73-7.64 (m, 15H), 6.12 (s, 1H), 5.73 (s, 1H), 4.23 (s, 2H), 4.11 (t, 2H), 2.36 (s, 2H), 2.03 (d, 2H), 1.85 (d, 2H), 1.69-1.82 (m, 6H), 1.63 (s, 3H), 1.55 (d, 2H).

$^{19}$F NMR (measurement solvent: deuterated chloroform, reference material: trichlorofluoromethane): δ=−114.58 (t, 2F).

Synthesis Example 3

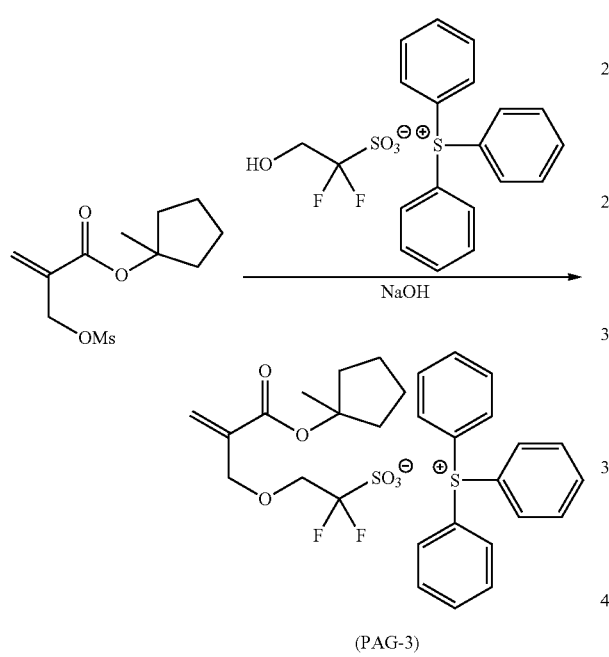

(PAG-3)

Synthesis of Target Compound (PAG-3)

In a 500-ml three-neck flask, 39.8 g (45.6 mmol) of an aqueous solution of 5% sodium hydroxide and 16.1 g (38.0 mmol) of 2-hydroxy-1,1-difluoroethanesulfonic acid triphenylsulfonium were placed. The resulting solution was stirred for 10 minutes at room temperature, thereby completely dissolving the solid substance. Subsequently, 20 g of crude 1-methylcyclopentyl 2-[(methanesulfonyloxy)methyl]acrylate was dropped and mixed into the solution. The mixed solution was then stirred for 1 hour at room temperature. After the completion of the reaction, the thus-obtained reaction solution was separated into an aqueous layer and a target product layer. The aqueous layer was extracted with 45 g of chloroform. The target product layer was combined with the chloroform extract. The combined product layer was washed five times with 45 g of water, washed twice with 30 g of 0.1N hydrochloric acid and further washed twice with 45 g of water. The washed product layer was concentrated under reduced pressure. With this, 26 g of the target compound (PAG-3) was obtained as a colorless oily substance (purity: 99%, yield: 77%).

<Properties of Target Compound (PAG-3)>

$^1$H NMR (measurement solvent: deuterated dimethyl sulfoxide, reference material: tetramethylsilane): δ=7.74-7.64 (m, 15H), 6.18 (s, 1H), 5.82 (s, 1H), 4.31 (s, 2H), 4.20 (t, 2H), 2.11 (m, 2H), 1.59 (m, 9H).

$^{19}$F NMR (measurement solvent: deuterated dimethyl sulfoxide, reference material: trichlorofluoromethane): δ=−114.03 (t, 2F).

[Production of Resins]

The structures and abbreviations of the compounds used in the following polymerization examples, working examples and comparative examples are indicated below.

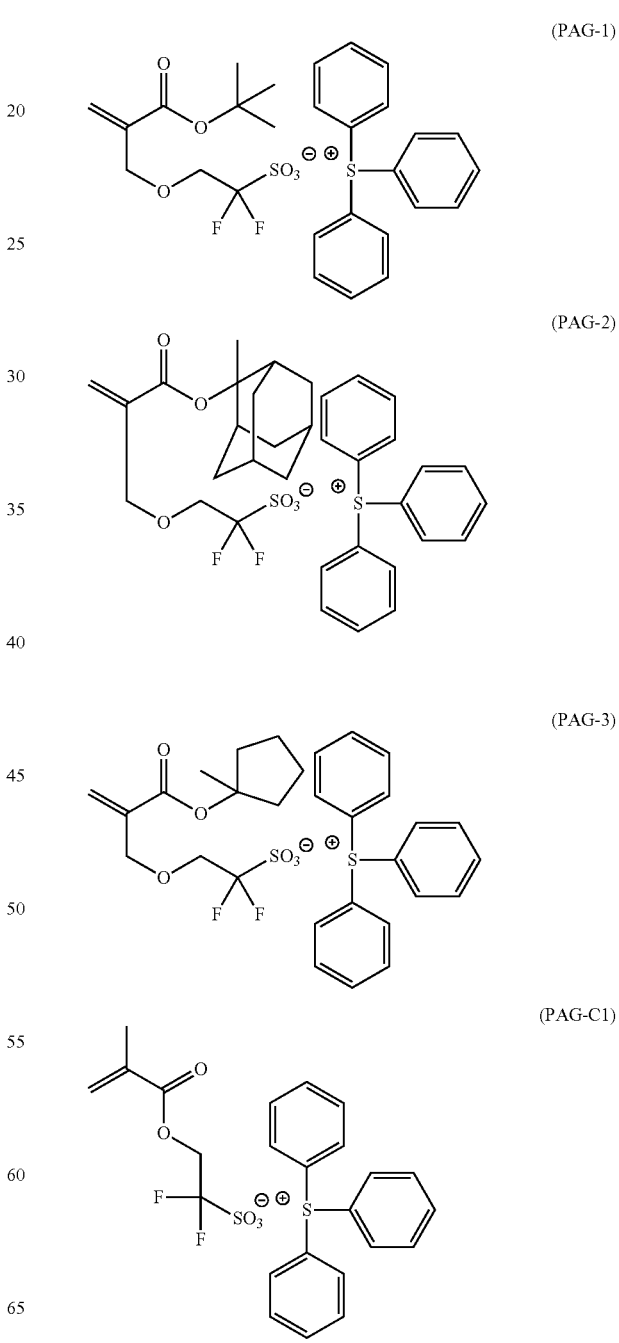

(PAG-C2) 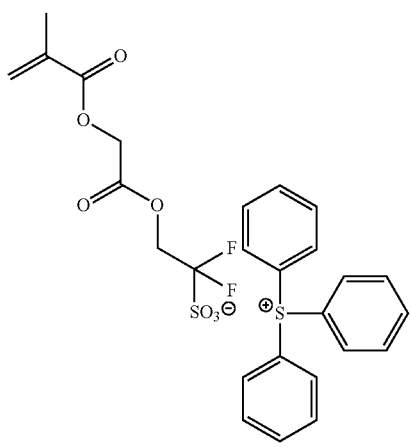
(A-1) 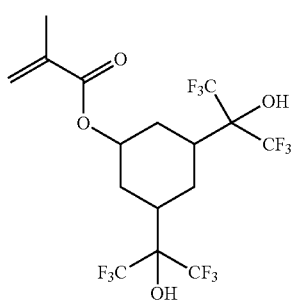
(A-2) 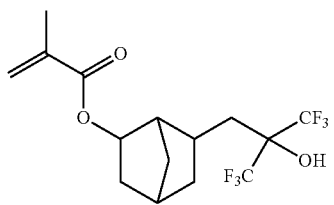
(A-3) 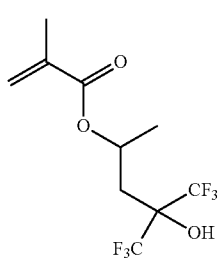
(A-4) 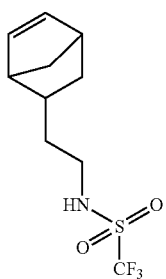
(A-5) 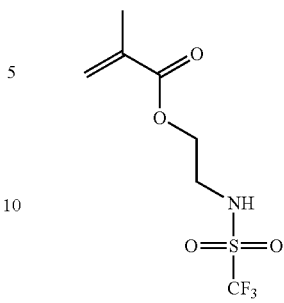
(A-6) 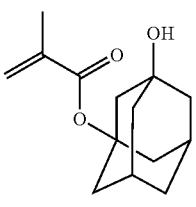
(A-7) 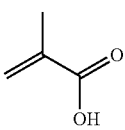
(B-1) 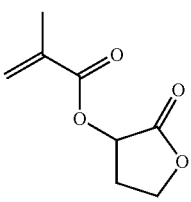
(B-2) 
(C-1) 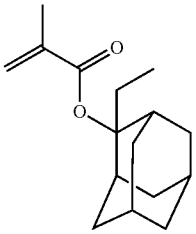

-continued

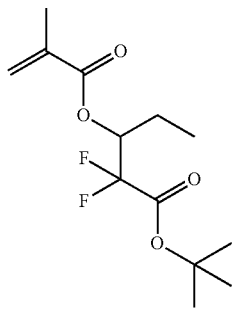

(C-2)

Polymerization Example P-1

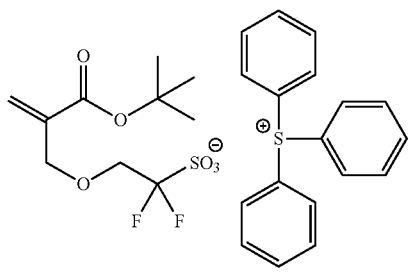

(PAG-1)

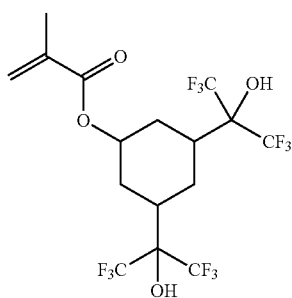

(A-1)

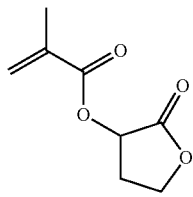

(B-1)

First, 3.4 g (40 mol %) of compound (PAG-1), 1.5 g (20 mol %) of compound (A-1), 1.02 g (40 mol %) of compound (B-1) and 0.12 g of n-dodecylmercaptan were dissolved in 5.9 g of 2-butanone. The resulting solution was admixed with 0.28 g of dimethyl 2,2'-azobis(2-methylpropionate), and then, heated to 85° C. with stirring under a nitrogen atmosphere. After stirring for 6 hours, the thus-obtained polymerization solution was cooled to about 25° C. by water cooling. The polymerization solution was dropped into 30 g of heptane, thereby precipitating a white powdery substance out of the solution. The precipitated powdery substance was filtered out, diluted twice with 5 g of acetone and reprecipitated with 30 g of water. The reprecipitated substance was filtered out and dried at 50° C. for 17 hours. With this, the target polymer was obtained in white powder form (5.0 g). The mass-average molecular weight (Mw) of the polymer was 7,300. Further, it was confirmed by $^{13}$C-NMR analysis that the polymer was in the form of a copolymer having repeating units derived from the compounds (PAG-1), (A-1) and (B-1) at a content ratio of 33.4:23.2:43.4 (mol %). This copolymer was named as "Resin (P-1)".

Polymerization Example P-2

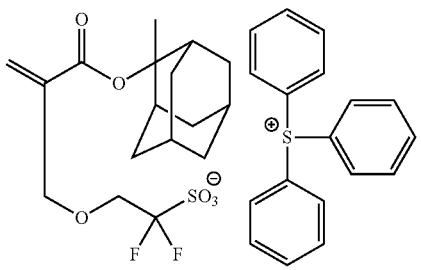

(PAG-2)

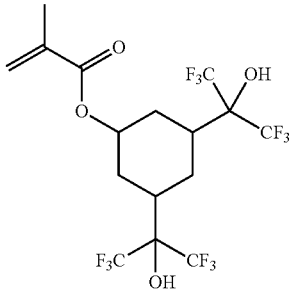

(A-1)

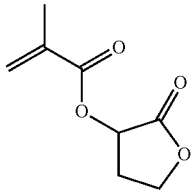

(B-1)

In 5.9 g of 2-butanone, 3.9 g (40 mol %) of compound (PAG-2), 1.5 g (20 mol %) of compound (A-1), 1.02 g (40 mol %) of compound (B-1) and 0.12 g of n-dodecylmercaptan were dissolved. The resulting solution was admixed with 0.28 g of dimethyl 2,2'-azobis(2-methylpropionate), and then, heated to 85° C. with stirring under a nitrogen atmosphere. After stirring for 7 hours, the thus-obtained polymerization solution was cooled to about 25° C. by water cooling. The precipitated powdery substance was filtered out, diluted twice with 5 g of acetone and reprecipitated with 30 g of water. The reprecipitated substance was filtered out and dried at 50° C. for 15 hours. With this, the target polymer was obtained in white powder form (4.7 g). The mass-average molecular weight (Mw) of the polymer was 7,100. Further, it was confirmed by $^{13}$C-NMR analysis that the polymer was in the form of a copolymer having repeating units derived from the compounds (PAG-1), (A-1) and (B-1) at a content ratio of 31.8:23.7:44.5 (mol %). This copolymer was named as "Resin (P-2)".

Polymerization Examples P-3 to P-24 and X-1 to X-6

Resins (P-3 to P-24 and X-1 to X-6) were produced in the same manner as in Polymerization Example P-1 or P-2. The kinds and contents of the copolymerization monomers, the mole ratio of the repeating units derived from the respective monomers and the mass-average molecular weight (Mw) of the produced resins are indicated in TABLES 1 and 2.

TABLE 1

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| P-1  | PAG-1 | 40 | A-1 | 20 | B-1 | 40 | — | — |
| P-2  | PAG-2 | 40 | A-1 | 20 | B-1 | 40 | — | — |
| P-3  | PAG-1 | 40 | A-1 | 20 | B-2 | 40 | — | — |
| P-4  | PAG-1 | 40 | A-2 | 20 | B-1 | 40 | — | — |
| P-5  | PAG-1 | 40 | A-3 | 20 | B-1 | 40 | — | — |
| P-6  | PAG-1 | 40 | A-4 | 20 | B-1 | 40 | — | — |
| P-7  | PAG-1 | 40 | A-5 | 20 | B-1 | 40 | — | — |
| P-8  | PAG-1 | 40 | A-6 | 20 | B-1 | 40 | — | — |
| P-9  | PAG-1 | 15 | A-6 | 25 | B-2 | 30 | C-1 | 30 |
| P-10 | PAG-1 | 15 | A-6 | 25 | B-2 | 30 | C-2 | 30 |
| P-11 | PAG-1 | 15 | A-1 | 25 | B-1 | 30 | C-1 | 30 |
| P-12 | PAG-1 | 15 | A-1 | 25 | B-1 | 30 | C-2 | 30 |
| P-13 | PAG-2 | 40 | A-1 | 20 | B-2 | 40 | — | — |
| P-14 | PAG-2 | 40 | A-2 | 20 | B-1 | 40 | — | — |
| P-15 | PAG-2 | 40 | A-3 | 20 | B-1 | 40 | — | — |
| P-16 | PAG-2 | 40 | A-4 | 20 | B-1 | 40 | — | — |
| P-17 | PAG-2 | 40 | A-5 | 20 | B-1 | 40 | — | — |
| P-18 | PAG-2 | 40 | A-6 | 20 | B-1 | 40 | — | — |
| P-19 | PAG-2 | 15 | A-6 | 25 | B-2 | 30 | C-1 | 30 |
| P-20 | PAG-2 | 15 | A-6 | 25 | B-2 | 30 | C-2 | 30 |
| P-21 | PAG-2 | 15 | A-1 | 25 | B-1 | 30 | C-1 | 30 |
| P-22 | PAG-2 | 15 | A-1 | 25 | B-1 | 30 | C-2 | 30 |
| P-23 | PAG-3 | 15 | A-1 | 25 | B-1 | 30 | C-1 | 30 |
| P-24 | PAG-3 | 15 | A-2 | 25 | B-1 | 30 | C-2 | 30 |

| Polymerization Example Resin | Mole ratio of repeating units in resin | | | | Molecular weight |
|---|---|---|---|---|---|
| | Monomer 1 | Monomer 2 | Monomer 3 | Monomer 4 | Mw |
| P-1  | 33 | 23 | 43 | — | 7,300 |
| P-2  | 32 | 24 | 44 | — | 7,100 |
| P-3  | 34 | 23 | 43 | — | 7,300 |
| P-4  | 30 | 24 | 46 | — | 8,500 |
| P-5  | 31 | 25 | 44 | — | 7,800 |
| P-6  | 32 | 22 | 46 | — | 8,700 |
| P-7  | 28 | 25 | 47 | — | 8,100 |
| P-8  | 34 | 22 | 44 | — | 8,600 |
| P-9  | 11 | 24 | 33 | 32 | 9,100 |
| P-10 | 8  | 27 | 32 | 33 | 8,300 |
| P-11 | 13 | 24 | 36 | 27 | 7,800 |
| P-12 | 10 | 21 | 36 | 33 | 7,300 |
| P-13 | 31 | 22 | 47 | — | 8,400 |
| P-14 | 35 | 24 | 41 | — | 8,900 |
| P-15 | 27 | 26 | 47 | — | 7,500 |
| P-16 | 30 | 22 | 48 | — | 8,100 |
| P-17 | 34 | 20 | 46 | — | 9,100 |
| P-18 | 29 | 26 | 45 | — | 8,800 |
| P-19 | 9  | 26 | 35 | 30 | 8,700 |
| P-20 | 13 | 23 | 33 | 31 | 7,900 |
| P-21 | 10 | 27 | 31 | 32 | 7,500 |
| P-22 | 8  | 22 | 37 | 33 | 7,800 |
| P-23 | 9  | 28 | 30 | 33 | 7,900 |
| P-24 | 10 | 25 | 34 | 31 | 7,700 |

Monomer 1: Polymerizable fluorine-containing sulfonic acid onium salt
Monomer 2, 3: Auxiliary monomer
Monomer 4: Monomer containing acid labile group

TABLE 2

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| X-1 | PAG-1 | 100 | — | — | — | — | — | — |
| X-2 | PAG-2 | 100 | — | — | — | — | — | — |

TABLE 2-continued

| | | | | | | | | |
|---|---|---|---|---|---|---|---|---|
| X-3 | PAG-3 | 100 | — | — | — | — | — | — |
| X-4 | PAG-1 | 50 | A-5 | 50 | — | — | — | — |
| X-5 | PAG-2 | 35 | — | — | — | — | C-1 | 65 |
| X-6 | PAG-3 | 35 | — | — | — | — | C-2 | 65 |

| Polymerization Example | Mole ratio of repeating units in resin | | | | Molecular weight |
|---|---|---|---|---|---|
| Resin | Monomer 1 | Monomer 2 | Monomer 3 | Monomer 4 | Mw |
| X-1 | 100 | — | — | — | 2,700 |
| X-2 | 100 | — | — | — | 3,200 |
| X-3 | 100 | — | — | — | 3,100 |
| X-4 | 45 | 55 | — | — | 7,800 |
| X-5 | 33 | — | — | 67 | 8,300 |
| X-6 | 33 | — | — | 67 | 8,100 |

Monomer 1: Polymerizable fluorine-containing sulfonic acid onium salt
Monomer 2, 3: Auxiliary monomer
Monomer 4: Monomer containing acid labile group Examples 1 to 33

Resist compositions were each prepared by mixing the above-produced resin with a solvent and other additive compounds. The component ratios of the prepared resist compositions are indicated in TABLES 3 and 4. Each of the prepared resist compositions was filtrated with a 0.2-μm membrane filter for the purpose of application. The kinds of the solvent, the additive (basic compound) and the cross-linking agent used in each example are indicated below.

Solvent
S-1: Propylene glycol monomethyl ether acetate (PGMEA)
S-2: γ-Butyrolactone
S-3: Ethyl lactate
S-4: Cyclohexanone
Basic compound
O-1: N,N-Dibutylaniline
O-2: 2,6-Diisopropylaniline
O-3: Diazabicyclo[4.3.0]nonene
O-4: 2,4,5-Triphenylimidazole
O-5: Trioctylamine
PAG: Nonafluorobutanesulfonic acid triphenylsulfonium (PAG-C3)

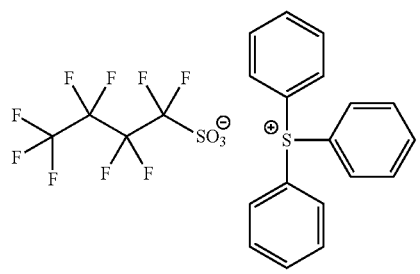

(PAG-C3)

[Pattern Formation]

Each of the above-obtained resist compositions was spin-coated on a silicon wafer substrate to form a resist film of 250 nm thickness. The resist film was prebaked at 110° C., exposed to 248-nm ultraviolet radiation through a photomask, and then, subjected to post exposure baking treatment at 120° C. After that, the resist film was developed with an aqueous solution of 2.38 mass % tetramethylammoniumhydroxide for 1 minute at 23° C. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLE 3.

TABLE 3

| Example | Resin 1 | | Resin 2 | |
|---|---|---|---|---|
| | Kind | parts by mass | Kind | parts by mass |
| 1 | P-1 | 40 | P'-1 | 20 |
| 2 | P-2 | 40 | P'-1 | 25 |
| 3 | P-3 | 40 | P'-5 | 20 |
| 4 | P-4 | 15 | P'-3 | 25 |
| 5 | P-5 | 40 | P'-3 | 25 |
| 6 | P-6 | 40 | P'-1 | 20 |
| 7 | P-7 | 15 | P'-3 | 25 |
| 8 | P-8 | 40 | none | — |
| 9 | P-9 | 40 | none | — |
| 10 | P-10 | 40 | none | — |
| 11 | P-11 | 40 | none | — |
| 12 | P-12 | 40 | none | — |
| 13 | P-13 | 40 | P'-3 | 20 |
| 14 | P-14 | 40 | P'-5 | 25 |
| 15 | P-15 | 40 | P'-3 | 20 |
| 16 | P-16 | 20 | P'-1 | 20 |
| 17 | P-17 | 20 | P'-5 | 20 |
| 18 | P-18 | 20 | none | — |
| 19 | P-19 | 40 | none | — |
| 20 | P-20 | 40 | none | — |
| 21 | P-21 | 40 | none | — |
| 22 | P-22 | 40 | none | — |
| 23 | P-23 | 40 | none | — |
| 24 | P-24 | 40 | none | — |
| 25 | X-1 | 4 | P'-1 | 40 |
| 26 | X-1 | 8 | P'-5 | 35 |
| 27 | X-2 | 4 | P'-1 | 40 |
| 28 | X-2 | 8 | P'-5 | 35 |
| 29 | X-3 | 4 | P'-1 | 40 |
| 30 | X-3 | 8 | P'-5 | 35 |
| 31 | X-4 | 12 | P'-3 | 35 |
| 32 | X-5 | 25 | P'-2 | 15 |
| 33 | X-6 | 25 | P'-2 | 15 |

| Example | Additive | Solvent | | Pattern shape |
|---|---|---|---|---|
| | | Kind | parts by mass | |
| 1 | O-1 | S-1 | 400 | clean rectangular shape |
| 2 | O-1 | S-1 | 400 | clean rectangular shape |
| 3 | O-1 | S-1 | 400 | clean rectangular shape |
| 4 | O-2 | S-2 | 400 | clean rectangular shape |
| 5 | O-3 | S-1 | 400 | clean rectangular shape |
| 6 | O-3 | S-1 | 400 | clean rectangular shape |

TABLE 3-continued

| | | | | |
|---|---|---|---|---|
| 7 | O-3 | S-1 | 400 | clean rectangular shape |
| 8 | O-1 | S-4 | 400 | clean rectangular shape |
| 9 | O-1 | S-2 | 400 | clean rectangular shape |
| 10 | O-4 | S-1 | 400 | clean rectangular shape |
| 11 | O-5 | S-1 | 400 | clean rectangular shape |
| 12 | O-5 | S-3 | 400 | clean rectangular shape |
| 13 | O-5 | S-1 | 400 | clean rectangular shape |
| 14 | O-5 | S-1 | 400 | clean rectangular shape |
| 15 | O-1 | S-1 | 400 | clean rectangular shape |
| 16 | O-1 | S-1 | 400 | clean rectangular shape |
| 17 | O-5 | S-1 | 400 | clean rectangular shape |
| 18 | O-3 | S-2 | 400 | clean rectangular shape |
| 19 | O-5 | S-1 | 400 | clean rectangular shape |
| 20 | O-5 | S-3 | 400 | clean rectangular shape |
| 21 | O-2 | S-1 | 400 | clean rectangular shape |
| 22 | O-3 | S-2 | 400 | clean rectangular shape |
| 23 | O-2 | S-1 | 400 | clean rectangular shape |
| 24 | O-3 | S-2 | 400 | clean rectangular shape |
| 25 | O-5 | S-1 | 400 | clean rectangular shape |
| 26 | O-5 | S-4 | 400 | clean rectangular shape |
| 27 | O-5 | S-3 | 400 | clean rectangular shape |
| 28 | O-5 | S-4 | 400 | clean rectangular shape |
| 29 | O-5 | S-1 | 400 | clean rectangular shape |
| 30 | O-5 | S-4 | 400 | clean rectangular shape |
| 31 | O-1 | S-1 | 400 | clean rectangular shape |
| 32 | O-1 | S-1 | 400 | clean rectangular shape |
| 33 | O-1 | S-1 | 400 | clean rectangular shape |

Basic compound (0.15 parts by mass)
O-1: N,N-Dibutylaniline, O-2: 2,6-Diisopropylaniline, O-3: Diazabicyclo[4.3.0]nonene
O-4: 2,4,5-Triphenylimidazole, O-5: Trioctylamine
Solvent
S-1: Propylene glycol monomethyl ether acetate (PGMEA), S-2: γ-Butyrolactone
S-3: Ethyl lactate, S-4: Cyclohexanone Reference Polymerization Example 1

Using various monomers, sulfonate-free, acid labile group-containing resins (P-1' to P-5') were produced as positive base resins in the same manner as in Polymerization Example 1 or 2. The mole ratio of the repeating units and the weight-average molecular weight (Mw) of the produced resins are indicated in TABLE 4.

TABLE 4

| Polymerization | Raw material composition | | | | | |
|---|---|---|---|---|---|---|
| Example | Monomer 1 | | Monomer 2 | | Monomer 3 | |
| Resin | Kind | mol % | Kind | mol % | Kind | mol % |
| P-1' | A-1 | 20 | B-1 | 45 | C-1 | 35 |
| P-2' | A-2 | 25 | B-1 | 45 | C-1 | 30 |
| P-3' | A-3 | 20 | B-1 | 45 | C-1 | 35 |
| P-4' | A-4 | 10 | B-1 | 45 | C-1 | 45 |
| P-5' | A-1 | 20 | B-1 | 45 | C-2 | 35 |

| Polymerization | | | | Molecular |
|---|---|---|---|---|
| Example | Mole ratio of repeating units in resin | | | weight |
| Resin | Monomer 1 | Monomer 2 | Monomer 3 | Mw |
| P-1' | 21 | 46 | 33 | 7,800 |
| P-2' | 24 | 46 | 30 | 8,500 |
| P-3' | 18 | 45 | 37 | 8,300 |
| P-4' | 11 | 44 | 45 | 7,900 |
| P-5' | 22 | 42 | 36 | 9,200 |

Reference Polymerization Example 2

Using various monomers including conventional onium salt monomers (PAG-C1, PAG-C2) in place of the polymerizable fluorine-containing sulfonic acid onium salts (polymerizable monomers) according to the present invention, resins (P-C1 to P-C4) each having an acid generating moiety on a side chain thereof were produced in the same manner as in Polymerization Example 1 or 2. The mole ratio of the repeating units and the weight-average molecular weight (Mw) of the produced resins are indicated in TABLE 5.

TABLE 5

| Polymerization | Raw material composition | | | | | | | |
|---|---|---|---|---|---|---|---|---|
| Example | Monomer 1 | | Monomer 2 | | Monomer 3 | | Monomer 4 | |
| Resin | Kind | mol % | Kind | mol % | Kind | mol % | Kind | mol % |
| P-C1 | PAG-C1 | 15 | — | — | B-1 | 45 | C-1 | 40 |
| P-C2 | PAG-C2 | 15 | — | — | B-1 | 45 | C-1 | 40 |
| P-C3 | PAG-C1 | 20 | A-6 | 30 | — | — | C-1 | 50 |
| P-C4 | PAG-C2 | 20 | A-6 | 25 | B-2 | 25 | C-1 | 30 |

| Polymerization | | | | | Molecular |
|---|---|---|---|---|---|
| Example | Mole ratio of repeating units in resin | | | | weight |
| Resin | Monomer 1 | Monomer 2 | Monomer 3 | Monomer 4 | Mw |
| P-C1 | 16 | — | 47 | 37 | 7,800 |
| P-C2 | 13 | — | 44 | 43 | 8,100 |
| P-C3 | 19 | 31 | — | 50 | 8,800 |
| P-C4 | 21 | 24 | 27 | 28 | 7,600 |

Monomer 1: Polymerizable fluorine-containing sulfonic acid onium salt (for reference use)
Monomer 2, 3: Auxiliary monomer
Monomer 4: Monomer containing acid labile group Comparative Examples 1 to 4

It was attempted to prepare resist compositions, in the same manner as in Examples 1 to 33, by mixing each of the resins produced from the conventional onium salt monomers with a solvent and additive compound. However, many of the resins were difficult to dissolve in propylene glycol monomethyl ether acetate (PGMEA) so that it was impossible to completely dissolve these resins even in twice as much volume of PGMEA. In the case of using cyclohexanone as the solvent, some of the resins were dissolved in the solvent. The thus-prepared resist compositions were subjected to pattern formation patterned in the same manner as in Examples 1 to 33. The component ratio and evaluation results of the resist compositions are indicated in TABLE 6.

TABLE 6

| Comparative Example | Resin 1 | | Additive | Solvent | | Pattern shape |
|---|---|---|---|---|---|---|
| | Kind | Parts by mass | | Kind | Parts by mass | |
| 1 | P-C1 | 40 | O-1 | S-1 | 400 | slightly stretched head shape |
| 2 | P-C1 | 40 | O-1 | S-4 | 800 | slightly distorted rectangular shape |
| 3 | P-C2 | 40 | O-1 | S-1 | 400 | slightly distorted rectangular shape |
| 4 | P-C2 | 40 | O-1 | S-4 | 800 | slightly stretched head shape |

Basic compound (0.15 parts by mass)
O-1: N,N-Dibutylaniline
Solvent
S-1: Propylene glycol monomethyl ether acetate (PGMEA), S-4: Cyclohexanone Examples 34 to 36

Using the resin P'-1 produced in Reference Polymerization Example 1 as a base resin and the polymerizable fluorine-containing sulfonic acid onium salts according to the present invention, as they were in monomer form, as a photoacid generator, resist compositions were prepared in the same manner as in Example 1 etc. The prepared resist compositions were patterned and observed in the same manner as in the other examples. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLE 7.

TABLE 7

| Example | Resin 1 | | Resin 2 | | Basic compound | Solvent | | Pattern shape |
|---|---|---|---|---|---|---|---|---|
| | Kind | parts by mass | Kind | parts by mass | | Kind | parts by mass | |
| 34 | P'-1 | 40 | PAG-1 | 4 | O-1 | S-1 | 400 | clean rectangular shape |
| 35 | P'-1 | 40 | PAG-2 | 4 | O-1 | S-1 | 400 | clean rectangular shape |
| 36 | P'-1 | 40 | PAG-3 | 4 | O-1 | S-1 | 400 | clean rectangular shape |

Basic compound (0.15 parts by mass)
O-1: N,N-Dibutylaniline
Solvent
S-1: Propylene glycol monomethyl ether acetate (PGMEA)

Industrial Applicability

The resin according to the present invention can be used as a photoacid generator for a photoresist material or can be used in itself as a positive resist resin. The monomer of such a resin is also useful as a raw material for production of other compounds.

The invention claimed is:

1. A polymerizable fluorine-containing sulfonic acid or sulfonate having an anion structure of the following general formula (1):

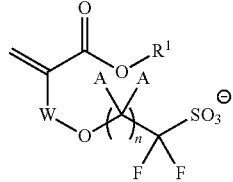

(1)

where
A each independently represent a hydrogen atom, a fluorine atom or a trifluoromethyl group;
n represents an integer of 1 to 10;
W represents a divalent linking group selected from the group consisting of substituted or unsubstituted methylene groups and substituted or unsubstituted divalent alicyclic hydrocarbon groups; or a divalent linking group formed by combination of one kind or two or more kinds selected from the group consisting of substituted or unsubstituted methylene groups and substituted or unsubstituted divalent alicyclic hydrocarbon groups;
any number of hydrogen atoms bonded to carbon atoms of the divalent linking group may be substituted with a fluorine atom;
any carbon atoms may form a ring with or without a substituent in the divalent linking group; and
$R^1$ represents an acid labile group.

2. The polymerizable fluorine-containing sulfonate according to claim 1, wherein the polymerizable fluorine-containing sulfonate is a polymerizable fluorine-containing sulfonic acid onium salt of the following general formula (2):

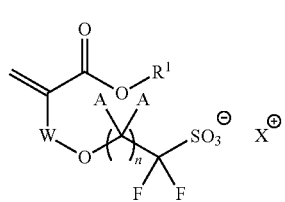

(2)

where A, n, W and $R^1$ have the same definitions as in the general formula (1); and $X^+$ represents either a sulfonium cation of the following general formula (a) or a iodonium cation of the following general formula (b):

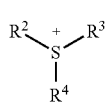

(a)

where R², R³ and R⁴ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of R², R³ and R⁴ may be bonded together to form a ring with a sulfur atom in the formula, $$R^5\text{—I}^+\text{—}R^6 \quad (b)$$

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula.

3. The polymerizable fluorine-containing sulfonate according to claim 2, wherein in the general formula (1), W is selected from the group consisting of one of the following linking groups —CH₂—    —CH₂CH₂—    —CH₂CH₂CH₂—
—CH₂CH(CH₃)—    —CH(CH₃)CH₂—    —(CH₂)₃—
—(CH₂)₄—    —(CH₂)₅—    —(CH₂)₆—    —(CH₂)₇—
—(CH₂)₈—    —CH₂—⟨cyclohexyl⟩—
—(CH₂)₃—⟨cyclohexyl⟩—    —(CH₂)₃—⟨cyclohexyl⟩—
—(CH₂)₄—⟨cyclohexyl⟩—    —(CH₂)₅—⟨cyclohexyl⟩—
—(CH₂)₆—⟨cyclohexyl⟩—    —(CH₂)₇—⟨cyclohexyl⟩—
—CH₂CH(CH₃)—⟨cyclohexyl⟩—
—CH(CH₃)CH₂—⟨cyclohexyl⟩—
—CH₂CH(C₂H₅)—⟨cyclohexyl⟩—
—CH(C₂H₅)CH₂—⟨cyclohexyl⟩—
—CH₂CH(CH₃)CH₂—⟨cyclohexyl⟩—
—(CH₂)₂CH(CH₃)CH₂—⟨cyclohexyl⟩—
—CH₂—⟨norbornyl⟩—    —(CH₂)₃—⟨norbornyl⟩—
—(CH₂)₃—⟨norbornyl⟩—    —(CH₂)₄—⟨norbornyl⟩—
—(CH₂)₅—⟨norbornyl⟩—    —(CH₂)₆—⟨norbornyl⟩—
—(CH₂)₇—⟨norbornyl⟩—
—CH₂CH(CH₃)—⟨norbornyl⟩—
—CH(CH₃)CH₂—⟨norbornyl⟩—
—CH₂CH(C₂H₅)—⟨norbornyl⟩—
—CH(C₂H₅)CH₂—⟨norbornyl⟩—
—CH₂CH(CH₃)CH₂—⟨norbornyl⟩—
—(CH₂)₂CH(CH₃)CH₂—⟨norbornyl⟩—
—CH₂—⟨adamantyl⟩—    —(CH₂)₃—⟨adamantyl⟩—
—(CH₂)₃—⟨adamantyl⟩—    —CH₂—⟨adamantyl⟩—
—(CH₂)₃—⟨adamantyl⟩—    —(CH₂)₃—⟨adamantyl⟩—.

4. A production method of a polymerizable fluorine-containing sulfonic acid onium salt of the general formula (2), comprising causing condensation of an acrylic acid derivative of the following general formula (15) and a hydroxyalkanesulfonic acid onium salt of the following general formula (16) in the presence of a base catalyst, $$\text{(15)}$$

where
W represents a divalent linking group selected from the group consisting of substituted or unsubstituted methylene groups and substituted or unsubstituted divalent alicyclic hydrocarbon groups; or a divalent linking group formed by combination of one kind or two or more kinds selected from the group consisting of substituted or unsubstituted methylene groups and substituted or unsubstituted divalent alicyclic hydrocarbon groups;

any number of hydrogen atoms bonded to carbon atoms of the divalent linking group may be substituted with a fluorine atom;

any carbon atoms may form a ring with or without a substituent in the divalent linking group;

$R^1$ represent an acid labile group; and

B represents a halogen atom or a leaving group,

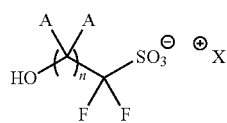
(16)

where A each independently represent a hydrogen atom, a fluorine atom or a trifluoromethyl group; n represents an integer of 1 to 10; $X^+$ represents either a sulfonium cation of the following general formula (a) or a iodonium cation of the following general formula (b):

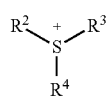
(a)

where $R^2$, $R^3$ and $R^4$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^2$, $R^3$ and $R^4$ may be bonded together to form a ring with a sulfur atom in the formula,

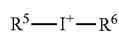
(b)

where $R^5$ and $R^6$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^5$ and $R^6$ may be bonded together to form a ring with a iodine atom in the formula,

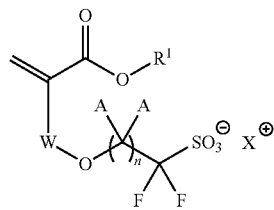
(2)

where A, n, W, $R^1$ and X' have the same definitions as in the general formulas (15) and (16).

5. The production method according to claim 4, wherein W is methylene in the general formulas (2) and (15).

6. The production method according to claim 4, wherein the acrylic acid derivative of the general formula (15) is of the following general formula (17) or (18):

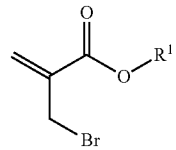
(17)

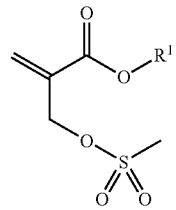
(18)

where $R^1$ has the same definition as in the general formula (15).

7. The production method according to claim 4, wherein the acrylic acid derivative of the general formula (15) is either tert-butyl 2-(bromomethyl)acrylate, 2-methyladamantyl 2-[(methanesulfonyloxy)methyl]acrylate or 1-methylcyclopentyl 2-[(methanesulfonyloxy)methyl] acrylate.

8. The production method according to claim 4, wherein n is 1 and A is hydrogen in the general formulas (2) and (16).

9. The production method according to claim 4, wherein $X^+$ is triphenylsulfonium in the general formulas (2) and (16).

10. The production method according to claim 4, wherein in the general formulas (2) and (15), W is selected from the group consisting of one of the following linking groups

—CH$_2$—    —CH$_2$CH$_2$—    —CH$_2$CH$_2$CH$_2$—

—CH$_2$CH(CH$_3$)—    —CH(CH$_3$)CH$_2$—    —(CH$_2$)$_3$—

—(CH$_2$)$_4$—    —(CH$_2$)$_5$—    —(CH$_2$)$_6$—

—(CH$_2$)$_7$—    —(CH$_2$)$_8$—

—CH$_2$—⬡—

—(CH$_2$)$_3$—⬡—    —(CH$_2$)$_3$—⬡—

—(CH$_2$)$_4$—⬡—    —(CH$_2$)$_5$—⬡—

—(CH$_2$)$_6$—⬡—    —(CH$_2$)$_7$—⬡—

—CH$_2$CH(CH$_3$)—⬡—

—CH(CH$_3$)CH$_2$—⬡—

—CH$_2$CH(C$_2$H$_5$)—⬡—

—CH(C$_2$H$_5$)CH$_2$—⬡—

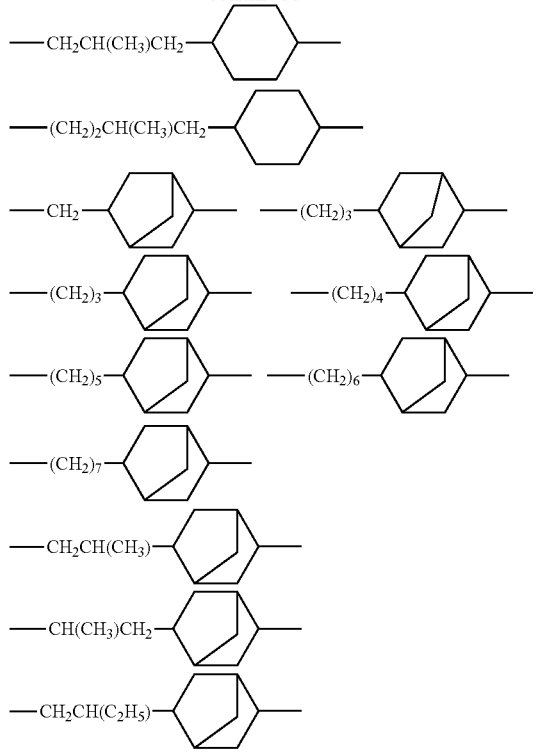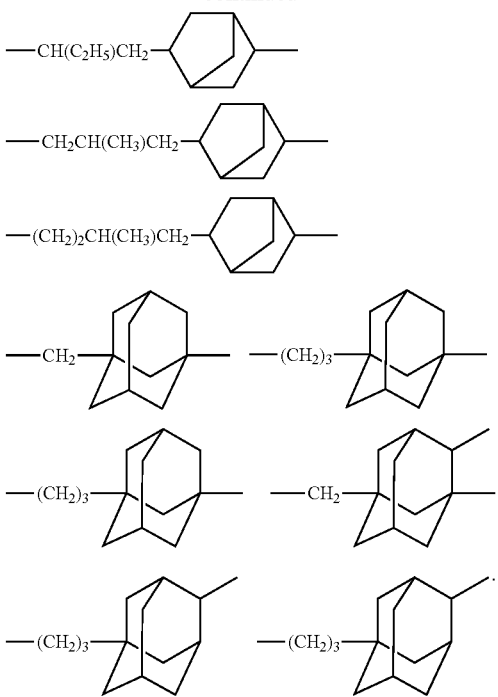
* * * * *